(12) United States Patent
Murphy et al.

(10) Patent No.: US 11,140,962 B2
(45) Date of Patent: Oct. 12, 2021

(54) LIQUID DERMATOLOGICAL AGENT DISPENSING DEVICE

(71) Applicant: RLM Group Ltd., Mt. Kisco, NY (US)

(72) Inventors: Robert L. Murphy, Mt. Kisco, NY (US); Charles A. Curtiss, Norwalk, CT (US)

(73) Assignee: RLM GROUP LTD., Mt. Kisco, NY (US)

( * ) Notice: Subject to any disclaimer, the term of this patent is extended or adjusted under 35 U.S.C. 154(b) by 0 days.

(21) Appl. No.: 16/890,487

(22) Filed: Jun. 2, 2020

(65) Prior Publication Data

US 2020/0288841 A1 Sep. 17, 2020

Related U.S. Application Data

(60) Division of application No. 16/180,779, filed on Nov. 5, 2018, now Pat. No. 10,702,040, which is a
(Continued)

(51) Int. Cl.
*B65D 47/42* (2006.01)
*A61F 13/40* (2006.01)
*A45D 34/00* (2006.01)

(52) U.S. Cl.
CPC ........... *A45D 34/00* (2013.01); *A61M 35/006* (2013.01); *B65D 47/42* (2013.01); *A45D 2200/054* (2013.01); *A45D 2200/058* (2013.01); *A45D 2200/1018* (2013.01); *A45D 2200/1036* (2013.01)

(58) Field of Classification Search
CPC ...... A45D 2200/1036; A45D 2200/058; A45D 2200/054; A45D 2200/1018; A45D 34/00; A45D 2200/00; A45D 2200/05; A45D 2200/10; A45D 2200/1009; A45D 2200/1045; B65D 47/44; B65D 47/42;
(Continued)

(56) References Cited

U.S. PATENT DOCUMENTS 4,446,965 A 5/1984 Montiel
4,772,148 A * 9/1988 Buschemeyer ...... A45D 34/042
401/206
(Continued)

FOREIGN PATENT DOCUMENTS

CN 1270786 A 10/2000
CN 1294080 A 5/2001
(Continued)

OTHER PUBLICATIONS

International Search Report and Written Opinion for International PCT Application No. PCT/US2018/060948, dated Feb. 27, 2019.
(Continued)

*Primary Examiner* — David J Walczak

(57) ABSTRACT

A dispensing device includes a container defining a reservoir containing a liquid and a porous applicator for dispensing the liquid. Another dispensing device includes two containers attached to each other, where the first container defines a reservoir containing a first liquid and a porous applicator for dispensing liquid and the second container contains a second liquid that may be dispensed via application of a force.

9 Claims, 37 Drawing Sheets

Figure 1A:
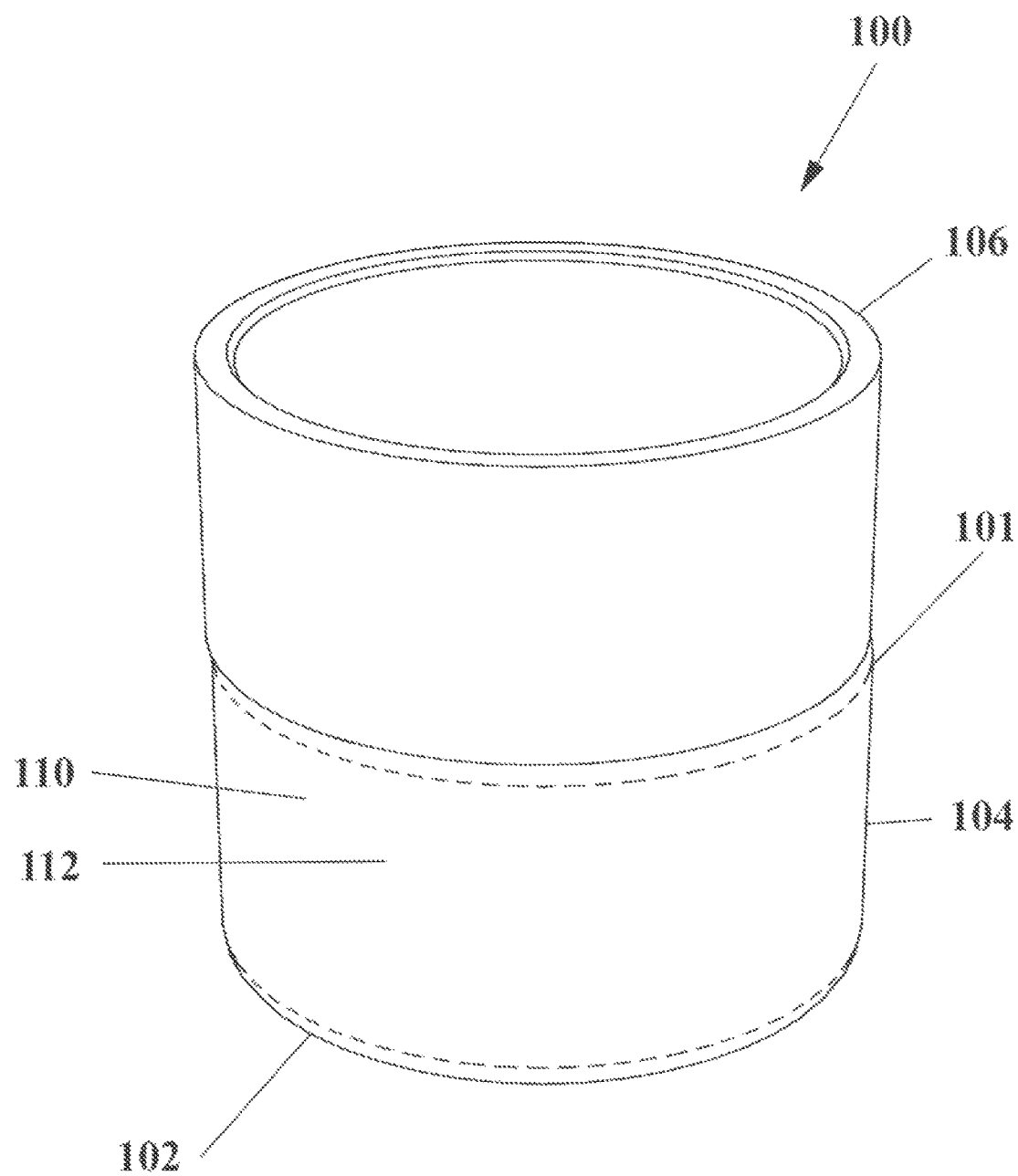

Related U.S. Application Data continuation-in-part of application No. 15/815,041, filed on Nov. 16, 2017, now Pat. No. 10,117,497.

(58) Field of Classification Search
CPC . A61M 35/003; A61M 35/006; B05C 17/002; B05C 17/00; A61F 13/15
USPC .................. 401/40–47, 265, 266; 15/104.93
See application file for complete search history.

(56) References Cited

U.S. PATENT DOCUMENTS

| | | |
|---|---|---|
| 4,932,802 A | 6/1990 | Cantone |
| 5,914,116 A | 6/1999 | Suares et al. |
| 6,457,891 B1 | 10/2002 | Bredacts |
| 6,491,041 B1 | 10/2002 | Okamoto |
| 6,497,527 B2 | 12/2002 | Kaufmann |
| 7,226,227 B2 | 6/2007 | Gueret |
| 7,686,528 B2 | 3/2010 | Gueret |
| 7,743,775 B2 | 6/2010 | Thiebaut |
| 7,845,871 B2 | 12/2010 | Thiebaut |
| 8,123,426 B2 | 2/2012 | Byun |
| 2002/0076256 A1 | 6/2002 | Gueret |
| 2004/0190974 A1 | 9/2004 | Cantone et al. |
| 2004/0234321 A1 | 11/2004 | Breidenbach et al. |
| 2006/0233590 A1 | 10/2006 | Thiebaut |
| 2006/0233594 A1 | 10/2006 | Erickson |
| 2011/0210039 A1 | 9/2011 | Alongi et al. |

FOREIGN PATENT DOCUMENTS

| | | |
|---|---|---|
| CN | 1350823 A | 5/2002 |
| CN | 1738558 A | 2/2006 |
| WO | 2019/099464 A1 | 5/2019 |

OTHER PUBLICATIONS

International Preliminary Report on Patentability for International PCT Application No. PCT/US2018/060948, dated Oct. 24, 2019.

\* cited by examiner

LIQUID DERMATOLOGICAL AGENT DISPENSING DEVICE

PRIORITY CLAIM

This application is a divisional application under 35 U.S.C. § 121 of currently U.S. application Ser. No. 16/180,779, filed Nov. 5, 2018, now U.S. Pat. No. 10,702,040, issued Jul. 7, 2020, which application claims priority under 35 U.S.C. § 120 as a continuation-in-part to U.S. application Ser. No. 15/815,041, filed Nov. 16, 2017, now U.S. Pat. No. 10,117,497, issued Nov. 6, 2018, which is incorporated herein by reference in its entirety.

BACKGROUND

Liquid dermatological agents, such as cosmetic or pharmaceutical creams, oils or serums, can be applied with many different types of delivery means, such as aerosol sprays, roll-ons, and pumps (which are also sometimes referred to as feeder systems); or a user could simply put their finger into the liquid to apply it. Some liquid dermatological agent dispensing devices, particularly ones with low-viscosity oil, serum, liquid dermatological agents, are prone to leakage, migrating or spilling, however.

SUMMARY

In one general aspect, the present invention is directed to a dispensing device that comprises a first container having a sidewall that defines a reservoir. The first container has an upper opening to the reservoir at a top of the first container. A first liquid, that comprises a dermatological agent, is in the reservoir, along with a porous applicator. The porous applicator comprises an injection-molded polyethylene body having open-celled pores that extend from a bottom of the porous applicator to a top surface of the porous applicator, such that the open-celled pores are filled with the first liquid such that the pores deliver the first liquid to the top surface of the porous applicator by capillary action without externally applied pressure, and such that the porous applicator substantially fills the reservoir and the upper opening at the top of the first container such that the first liquid is prevented from free-flowing out of the reservoir. As such, the porous applicator can deliver the first liquid to the top surface of the porous applicator without use of a pump or buffer. Additionally, as such, the porous applicator may advantageously reduce or prevent migration of low viscosity liquids such as oils or serums.

In other embodiments, the dispensing device comprises a second container, e.g., a squeeze tube, containing a second liquid that may comprise a second dermatological agent that is different from the first liquid. The second container may have a circular, threaded post at an upper end of the second container; and the first container may comprise a circular post that extends upward from a lower, central portion of the first container into the reservoir. The circular post of the first container may comprise a downward-facing threaded recess for receiving the threaded post of the second container such that first container is detachably removable from the second container by unscrewing the first container.

In various implementations, the circular post of the first container comprises an upper wall that blocks the second liquid from entering the reservoir defined by the first container. In other embodiments, the threaded post of the second container comprises a tip that extends from the threaded post of the second container into the porous applicator when the first container is attached to the second container. In such embodiments, the tip can comprise an opening for dispensing the second liquid that is in the second container. The upper (or distal) end of the tip can terminate below or at the top surface of the porous applicator when the threaded post of the second container is fully threaded into the circular post of the first container. Also, the cap can comprise a downward facing pintle that is inserted into the opening of the tip of the second container when the cap is attached to the first container and the threaded post of the second container is fully threaded into the circular post of the first container.

In other embodiments, the second container contains a powder, such as a glitter. Also, the top surface of the porous applicator can have a dome shape, and the dispensing device may comprise a lid that is removably coupled to the first container and that has a shape that corresponds to a shape of the porous applicator. The lid may define a space between a top portion of the lid and the top surface of the porous applicator such that upon the second container receiving a squeezing force, the powder (e.g., glitter) is squeezed into and dispersed about the space. That way, a user could remove the lid to simultaneously apply the powder and the liquid in the porous applicator. Moreover, the lid may comprise a pintle and a knob for controlling the coupling of the lid to the first container.

In additional embodiments, the first container has one or more interior walls in addition to having a sidewall so that the sidewall and one or more interior walls define a plurality of reservoirs, including a first reservoir and a second reservoir. In such embodiments, a liquid dermatological agent and the porous applicator could be in the first reservoir, and another dermatological agent, such as a cream that complements or supplements the liquid dermatological agent, could be in the second reservoir. A user could use their fingers to apply either dermatological agent simply by touching the porous applicator or the cream, at the user's choosing. The porous applicator may define a dome for controlling a dosage of the first liquid dispensed by the dispensing device. Moreover, the porous applicator may define a trough area around the dome.

In other embodiments, the dispensing device comprises a plastic bag that contains a liquid dermatological agent. The bag comprises a closed distal end and an opening at a proximate end. The porous applicator may be inserted into the opening at the proximate end of the plastic bag such that: the porous applicator has an upper portion that extends past a top of the proximate end of the plastic bag; the porous applicator draws the liquid in the plastic bag by way of a vacuum such that the open-celled pores of the porous applicator are filled with the liquid dermatological agent such that the pores deliver the liquid to a top surface of the porous applicator by capillary action; and the porous applicator substantially fills the opening at the proximate end of the plastic bag, to help create the vacuum, such that the liquid is prevented from free-flowing out of the plastic bag. The plastic bag may comprise high-density polyethylene, low-density polyethylene, and/or linear low-density polyethylene. Also, the dispensing device can comprise a rigid container containing the plastic bag and (at least partially) the porous applicator. The dispensing device may also comprise a cap that is removably coupled to the rigid container such that: when the cap is coupled to the rigid container, the rigid container is sealed and the vacuum is present; and when the cap is decoupled from the rigid container, a vent of the rigid container is exposed.

In yet other embodiments, the dispensing device comprises a first liquid dermatological agent in the reservoir and the porous applicator is saturated with a second dermatological agent such that the open-celled pores of the porous applicator are filled with the second dermatological agent such that the pores deliver the second dermatological agent to the top surface of the porous applicator by capillary action. The porous applicator is inserted in an opening at the top end of the first container and defines an opening from a bottom surface of the porous applicator to the top surface of the porous applicator, such that the first dermatological agent can flow through the opening in the porous applicator to the top surface of the porous applicator. That way, a user can simultaneously apply the first and second dermatological agents by, for example, squeezing the dispensing device so that the first dermatological agents flow through the opening in the porous applicator to the top surface of the porous applicator, and applying the porous applicator, with the second dermatological agent, to the user's skin. The second dermatological agent may form a lubricating layer or other type of enhancer over which the first dermatological agent flows.

The first and second liquid dermatological agents can be cosmetic or pharmaceutical dermatological agents, such as cosmetic or pharmaceutical creams, oils, lotions, fragrances, etc.

These and other benefits and features of the present invention will be apparent from the description below.

FIGURES

Figure 11:
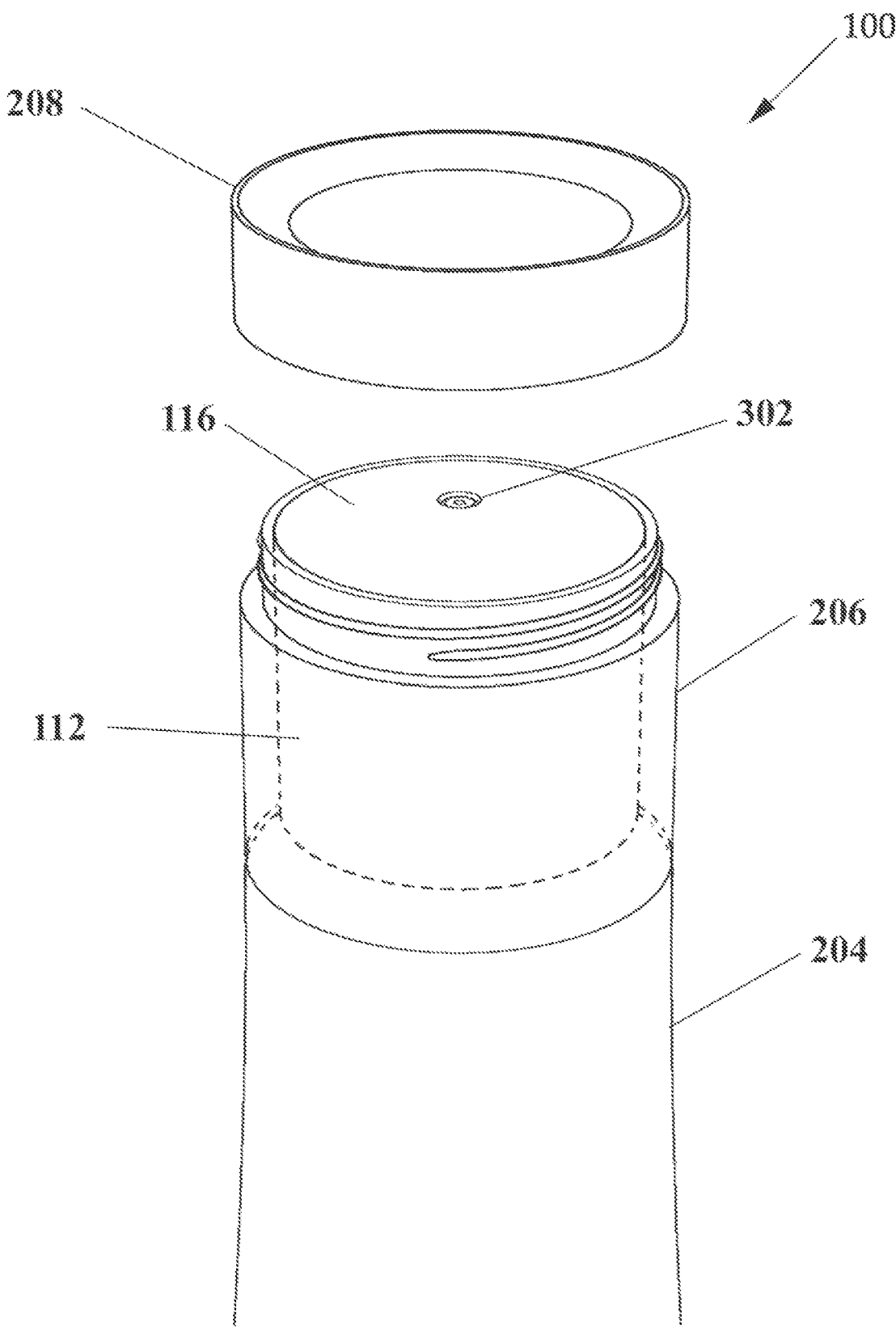
Figure 12:
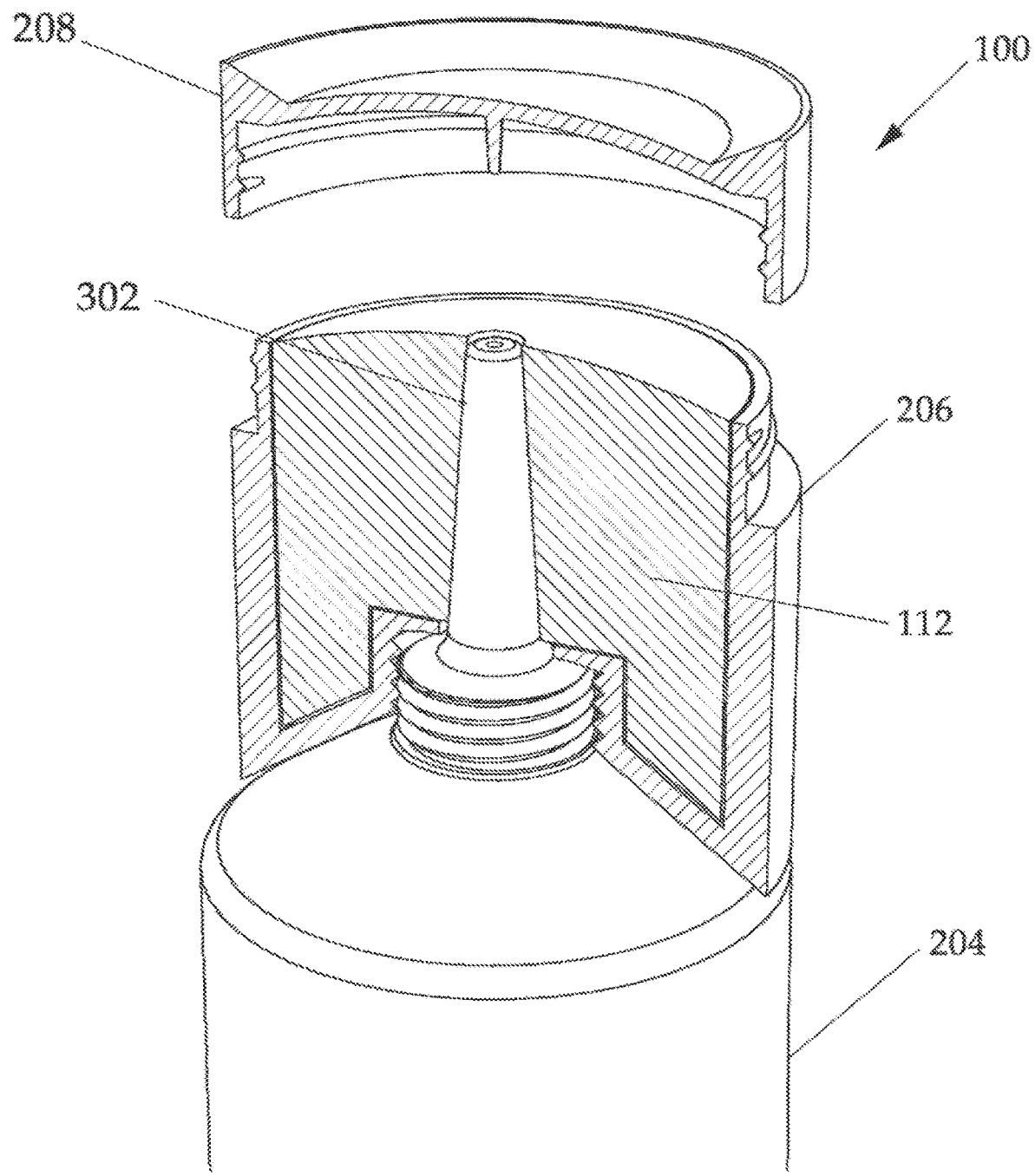

Various embodiments of the present invention are described herein by way of example in connection with the following figures, wherein:

FIGS. 1A-1C and 2 illustrate an example dispensing device that includes a porous applicator according to various embodiments of the present invention;

FIGS. 3, 4, 5A-5B, 6, and 7A-7C are views of an example dispensing device in a dual container configuration according to various embodiments of the present invention;

FIGS. 8A-8B, 9A-9B, and 10A-10B are views of an example dispensing device in a dual container configuration according to other various embodiments of the present invention;

FIGS. 11 and 12 are views of an example dispensing device in a dual container configuration according to still other various embodiments of the present invention.

FIGS. 13A-13B, 14, 15A-15B, and 16 are views of an example dispensing device in a fountain configuration according to various embodiments of the present invention.

FIGS. 17A-17B, 18-20, and 21A-21B are views of an example dispensing device in an interior wall configuration according to various embodiments of the present invention.

FIGS. 22A-22B and 23A-23B are views of an example dispensing device in a bag-feed vacuum configuration according to various embodiments of the present invention.

FIGS. 24A-24C, 25A-25B, 26A-26B, and 27 are views of an example dispensing device in a pre-saturated porous applicator configuration according to various embodiments of the present invention.

DESCRIPTION

In one general aspect, the present invention is directed to a dispensing device that dispenses fluids, particularly dermatological agents, such as cosmetic, fragrance or pharmaceutical liquids or serums via a porous applicator. The porous applicator preferably prevents the liquid within the dispensing device from free flowing (e.g. spilling) out of the device. In various embodiments, the porous applicator delivers the liquid to the top surface of the porous applicator via capillary action. That is, for example, the porous applicator, which can form a pad or dome for easy application of the dermatological agent, wicks the liquid in the container to the top surface of the porous applicator. A user can apply the porous applicator directly to the desired skin area to dispense the liquid to the desired skin area; or the user could collect a desired amount of the liquid from the porous application on a finger or tool, and then apply the liquid to the desired skin area with the finger or tool, for example. As liquid is dispensed via the porous applicator, additional liquid of the dispensing device wicks upwards to the top surface to replenish the top surface of the porous applicator. One advantage of the dispensing device is that it facilitates the controlled application of the liquid dermatological agent while reducing or even preventing leaking or spilling. Another advantage is that dispensing device does not require a pump or buffer to deliver the liquid dermatological agent, thereby simplifying the manufacturer and operation of the dispensing device. In other words, the dispensing device does not require, and preferably does not include, a separate buffer or sealing layer for protecting against leakage that could be caused by displacement of the dispensing device. That is, for example, if a user of the dispensing device displaces the dispensing device to a 90 degree angle via accidental contact, the self-sealing porous applicator will prevent liquid dermatological agent from leaking past the top surface.

Figure 1B:
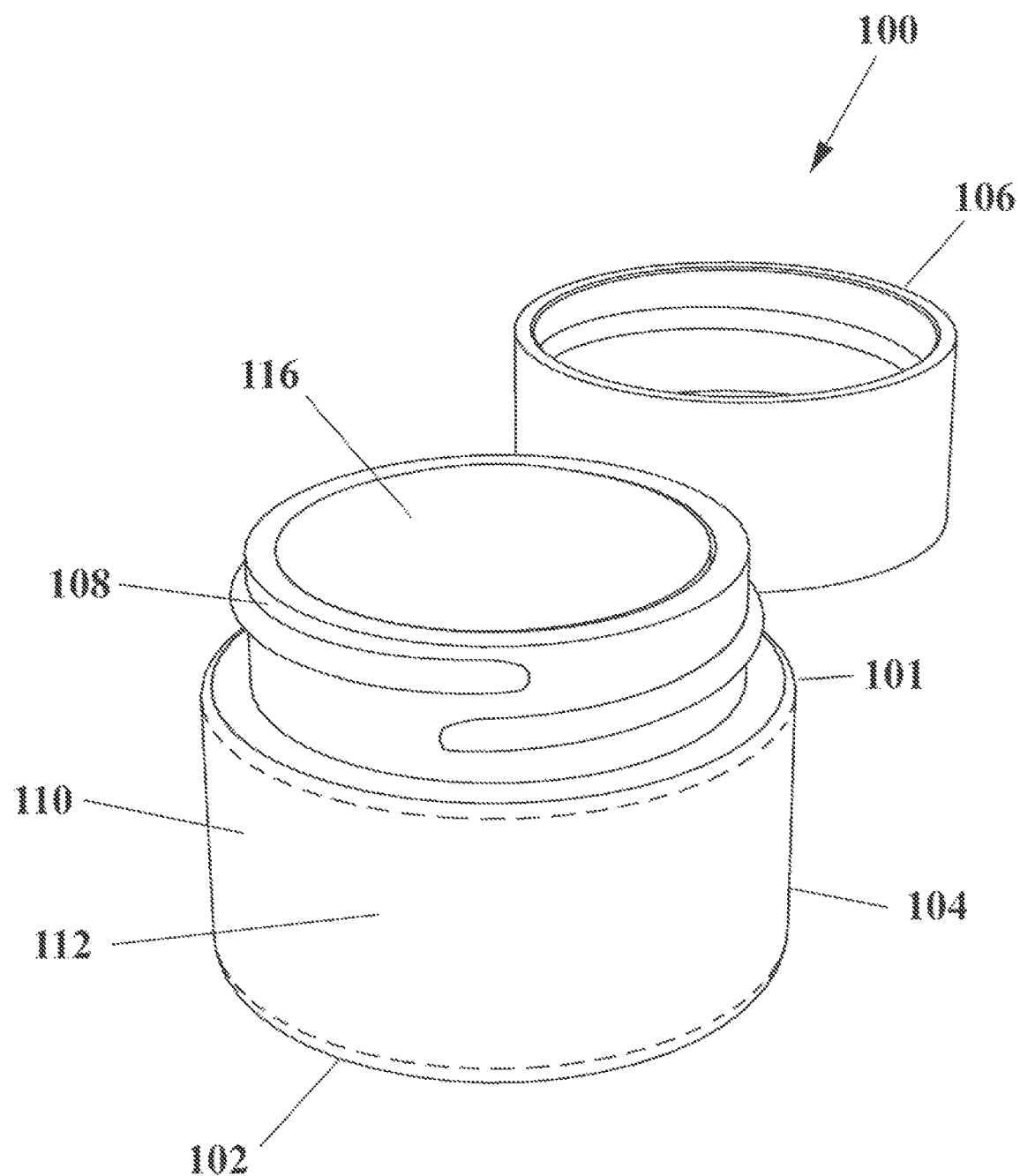
Figure 1C:
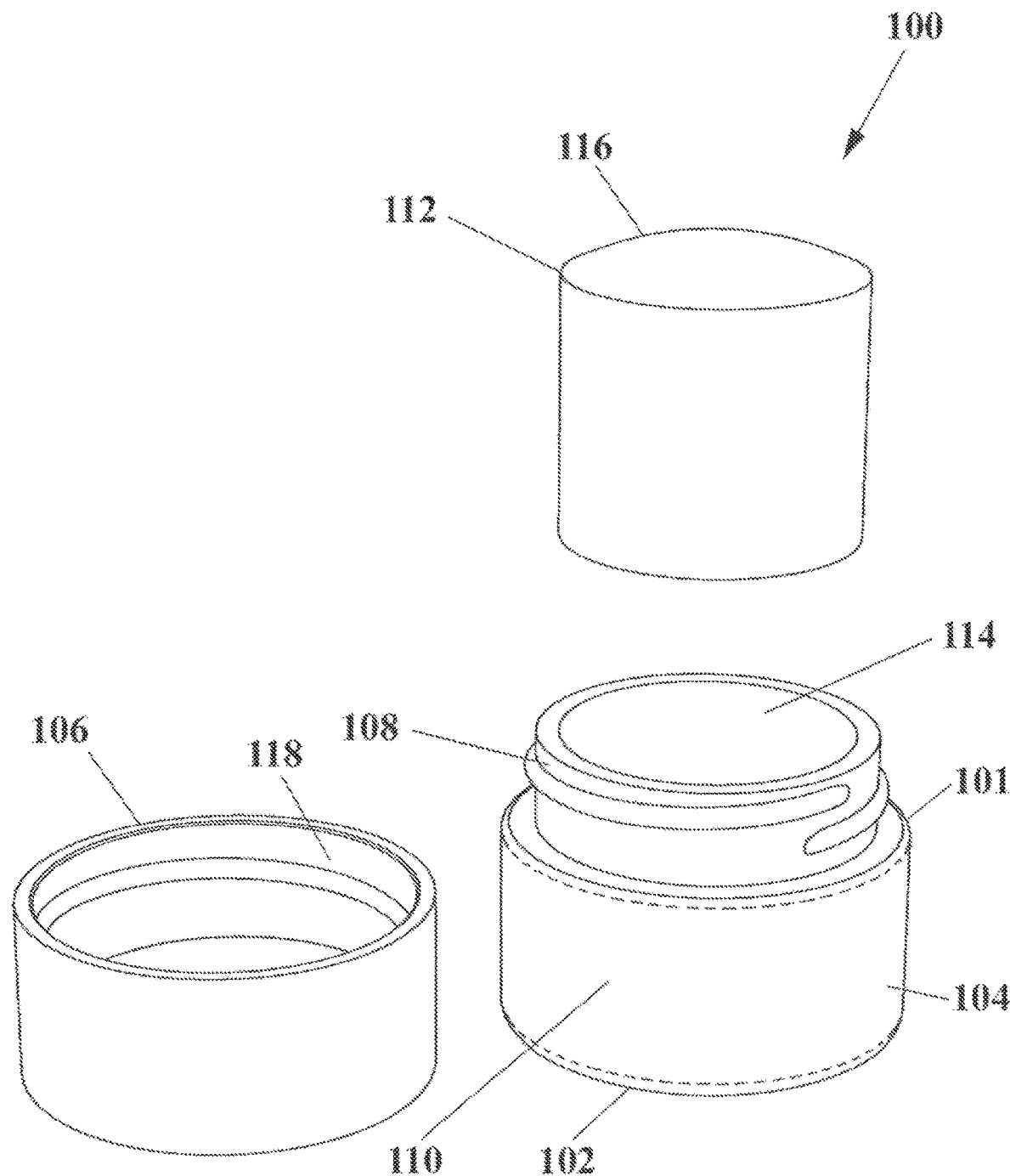

FIGS. 1A, 1B and 1C show a dispensing device 100 according to various embodiments of the present invention. As shown in these figures, the dispensing device 100 comprises a container 101, a porous applicator 112 in the container 101, and a cap 106. FIG. 1A shows the cap 106 connected to the container 101; FIG. 1B shows the cap 106 unconnected from the container 101; and FIG. 1C shows the cap 106 unconnected from the container 101 and the porous applicator 112 removed from the container 101.

The liquid dermatological agent is placed in the container 101 with the porous applicator 112. In the illustrated embodiment, the container 101 is a cylindrical container, although in other embodiments other three dimensional structures could be used, such as a rectangular prism. The container 101 comprises a bottom surface 102 and an annular sidewall 104 extending upward therefrom, which collectively define a reservoir 110 in which the liquid and porous applicator 112 are placed. The cap 106 preferably is detachably removable from an upper lip 108 of the sidewall 104 of the container 101. For example, the cap 106 could snap-fit to the upper lip 108 or, as shown in FIG. 1B, the cap 106 and upper lip 108 may comprise mating threaded portions so that cap 106 can be removably threaded to the container 101 through rotation of the cap 106 relative to the container 101 and upper lip 108.

The porous applicator 112 may be any suitable porous material that wicks the liquid dermatological agent in the container 101 through capillary action from the container 101 to a top surface 116 of the porous applicator 112 so that the liquid can be applied to a desired skin region of a user of the dispensing device 100. In various embodiments, the porous applicator 112 may comprise POREX® porous plastics, porous polymer fibers, and/or porous foam. POREX® is a trademark of Porex Corporation. The porous plastics can comprise various polymers including ultra-high molecular weight polyethylene (UHMWPE), high-density polyethylene (HDPE), polypropylene (PP), polytetrafluoroethylene (PTFE), polyvinylidene fluoride (PVDF), ethylene vinyl acetate (EVA), polyethersulfone (PES), polyurethane (PU) and/or PE/PP co-polymer as base materials. The porous polymer fibers can comprise polyester core fiber (PE/PET) fiber or bicomponent polyester sheath and polyester core fiber (PET/PET fiber). A synthetic fiber binding process can be used to extrude various profile polymer fiber geometries with various density, permeability, and wicking performance requirements. In addition, other polymer fibers such as polyolefins, nylon, cellulosic, acetate and other fibers may be blended and bonded together with PE/PET or PET/PET fiber. The porous foam can be polyurethane foam manufactured through a hydrophilic or hydrophobic polyurethane process. Such porous materials comprise pores with interconnected cavities such that fluidic communication throughout each porous material is enabled, thereby enabling the liquid in the container 101 to be delivered to the top surface 116 of the porous applicator 112. For example, porous polymer fibers are utilized to produce wicking media with open-cell pore structures that control liquid volume capacity and liquid transfer rates. The size of the pores of the porous materials varies depending on the material used. For example, the pore size diameters range from: 7 to 150 micrometers (mm) and up to 300 mm for PE, 80 to 150 mm for PP, 2 to 100 mm for polymer fibers, and 90 to greater than 350 mm for porous foam.

As mentioned above, the annular sidewall 104 may define a reservoir 110 containing the liquid. The liquid can be a dermatological agent, such as a cleansing agent, serum, cream, astringent, topical corticosteroid, emollient, exfoliator, skin treatment, or other suitable dermatological agent. For example, the dermatological agent can be a skin moisturizing cream or a skin pharmaceutical. The reservoir 110 may be coextensive with the internal volume of container 101. The annular sidewall 104 can also comprise an upper lip 108 that extends upward to define an upper opening for the container 101. In various embodiments, such as the embodiment shown in FIGS. 1A-1C, the upper opening is the only opening to the container 101. The cap 106 can comprise a correspondingly downward facing inner sidewall 118 configured to engage the upper lip 108 of the container 101 in a friction fit or threaded engagement, according to various embodiments. In this way, the cap 106 is attachable and detachable from the container 101. When the cap 106 is detachably removed from the container 101, the porous applicator 112 becomes visible and accessible to a user so that the liquid dermatological agent in the container 101 can be applied to the desired skin area via the top surface 116 of the porous applicator 112.

Preferably, the porous applicator 112 is positioned within the reservoir 110 and substantially fills the reservoir 110 such that the liquid in the container 101 is prevented from free-flowing out of the reservoir 110. Thus, the liquid may be dispensed from the dispensing device 100 without leaking. Prevention of liquid free flow is achieved based on the porous applicator 112 substantially filling the space defined by the reservoir 110 and a top surface 116 of the porous applicator 112 substantially filling the upper opening 114 of the container 101. This positioning of the porous applicator 112 in the container 101 creates a vacuum by absorption of the liquid by the pores of the porous applicator 112 that prevents the liquid from leaking out of the reservoir 110. As liquid absorption occurs by the porous applicator 112, the volume of the pores of the porous applicator increase, resulting in a corresponding decrease of the pressure within the pores according to Boyle's Law. Thus, the pores located at the topmost portion of the porous pad 112 have a lower pressure than the pressure of the air molecules at the top of the porous applicator 112. This results in a net inward force at the top surface 116 of the porous applicator 112 at the opening 114, which reduces or prevents leakage or spilling as liquid from the container 101 is dispensed via the porous applicator 112. In other words, liquid absorption of the pores creates a vacuum within the container 101. The vacuum slows the capillary flow of the liquid upwards and reduces or prevents leaking.

As shown in FIG. 1C, the shape of the porous applicator 112 preferably conforms to the internal volume of the container 101 such that the porous applicator 112 substantially fills the entire space defined by the reservoir 110 (i.e., fills the reservoir 110 enough to prevent leakage). Hence, in the embodiment shown in FIG. 1C, the porous applicator 112 is cylindrically shaped to match the shape of the container's reservoir 110. Thus, the porous applicator 112 fits snugly into the container 101. This can be advantageous because the porous applicator 112 can be easily inserted into the container 101 and remain in the inserted position without undesirable movement.

A user may comfortably access the liquid within the dispensing device 100 at the top surface 116 of the porous applicator 112 without external dripping or spilling of the liquid. As shown in FIG. 1C, the top surface 116 can have a convex curvature for direct application of the liquid by the user. In other embodiments, the top surface 116 could be flat or concave or some other desired profile. In other embodiments, the container 101 may comprise multiple compartments, with the porous applicator 112 and first liquid in one (or more) of the compartments. Another liquid dermatological agent (e.g., a cream) could be in another compartment, without the porous applicator, so that it is applied without a porous applicator.

Figure 2:
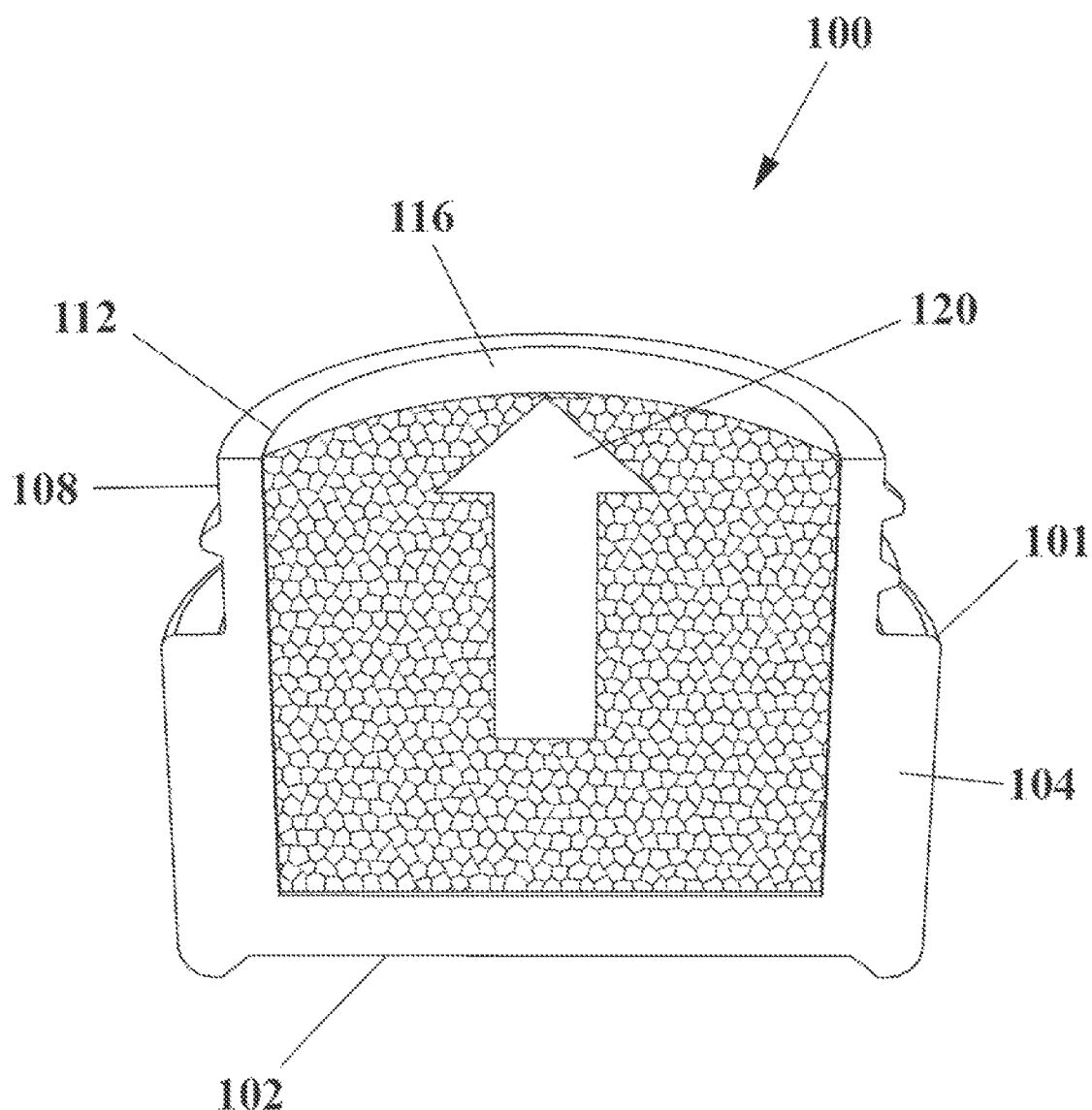

FIG. 2 is a cross section view of the dispensing device 100 according to various embodiments of the present invention. The cross section view illustrates the capillary action of the porous applicator 112. In various embodiments, a suitable molding process such as injection molding is used to mold the porous applicator 112 such that the porous applicator 112 comprises a plurality of open celled pores of varying sizes. In one embodiment, the varying size pores form a gradient such that the pore sizes are largest at the bottom of the porous applicator 112 and gradually decrease in size to the smallest pore sizes at the top surface 116 of the porous applicator 112. Accordingly, the liquid in the container 101 wicks upwards from the larger pores to the small pores, as denoted by the arrow 120. The pore size gradient contributes to the creation of the vacuum within the container 101. Specifically, larger pores absorb a relatively greater volume of liquid than absorbed by smaller pores. Consequently, when temperature is constant, according to Boyle's Law, the larger pores experience a corresponding relatively larger decrease in pressure than the smaller pores. Because the smaller pores have a relatively higher pressure than the larger pores, there is a corresponding force applied from the top surface 116 towards the bottom of the dispensing device 100, according to the progressively decreasing size of the pores from bottom to the top. This force resists the capillary action of the liquid, causing the capillary flow of the liquid to slow down. Leakage of the liquid out of the dispensing device 100 is prevented or reduced based on this inward force applied at the surface of the single opening 114.

The capillary action may be continuous such that the liquid continuously wicks upward to the pad 116 when there are pores available to absorb the liquid. Specifically, as a user dispenses the liquid by contacting the top surface 116 or the porous applicator, liquid is removed from the porous applicator, which is replenished based on the capillary action moving additional liquid to the top surface 116 of the porous applicator 112. Because the user contact for dispensing liquid removes liquid from the pores at the top surface 116, the volume increase caused by absorption is reversed and the volume of such top surface 116 pores decreases. As a result, pressure of the top surface pores increases, and the vacuum within the container 101 is temporarily released. When the top surface pores are replenished based on the continuous capillary action, the smaller top surface pores again absorb a relatively lesser volume of liquid and consequently have a greater pressure than the larger pores below the top surface 116. Thus, the vacuum is recreated as discussed above. The cycle of vacuum creation and release may advantageously enable continuous priming or supplying liquid to the pad 116 for dispensing liquid to the user, without leaks or spilling.

In addition, the porosity or wicking ability of the porous applicator 112 can be selected based on the liquid in the first container, since low viscosity liquids wick more easily than high viscosity liquids. Where the liquid is sufficiently viscous that the porous applicator can wick it continuously without additional external force, the container 101 could be made of a hard, rigid material, such as hard, rigid plastic, such as injection-molded or extruded high-density polyethylene (HDPE), which may be opaque or transparent. Where, however, the liquid is too viscous for the porous applicator alone to wick it without external forces, the container 101 could be made of a flexible, pliable material, such as a flexible, pliable plastic, so that the user could squeeze the container 101 to help force the liquid to the top surface 116 of the porous applicator 112. In this way, the combination of the capillary action from the porous applicator and an external force applied to the pliable container 101 by the user can enable the liquid to move to the top surface 116. Moreover, where the container 101 is made of pliable material, the porous applicator 112 can comprise a hydrophilic material for encouraging capillary flow of the porous applicator 112.

Figure 3:
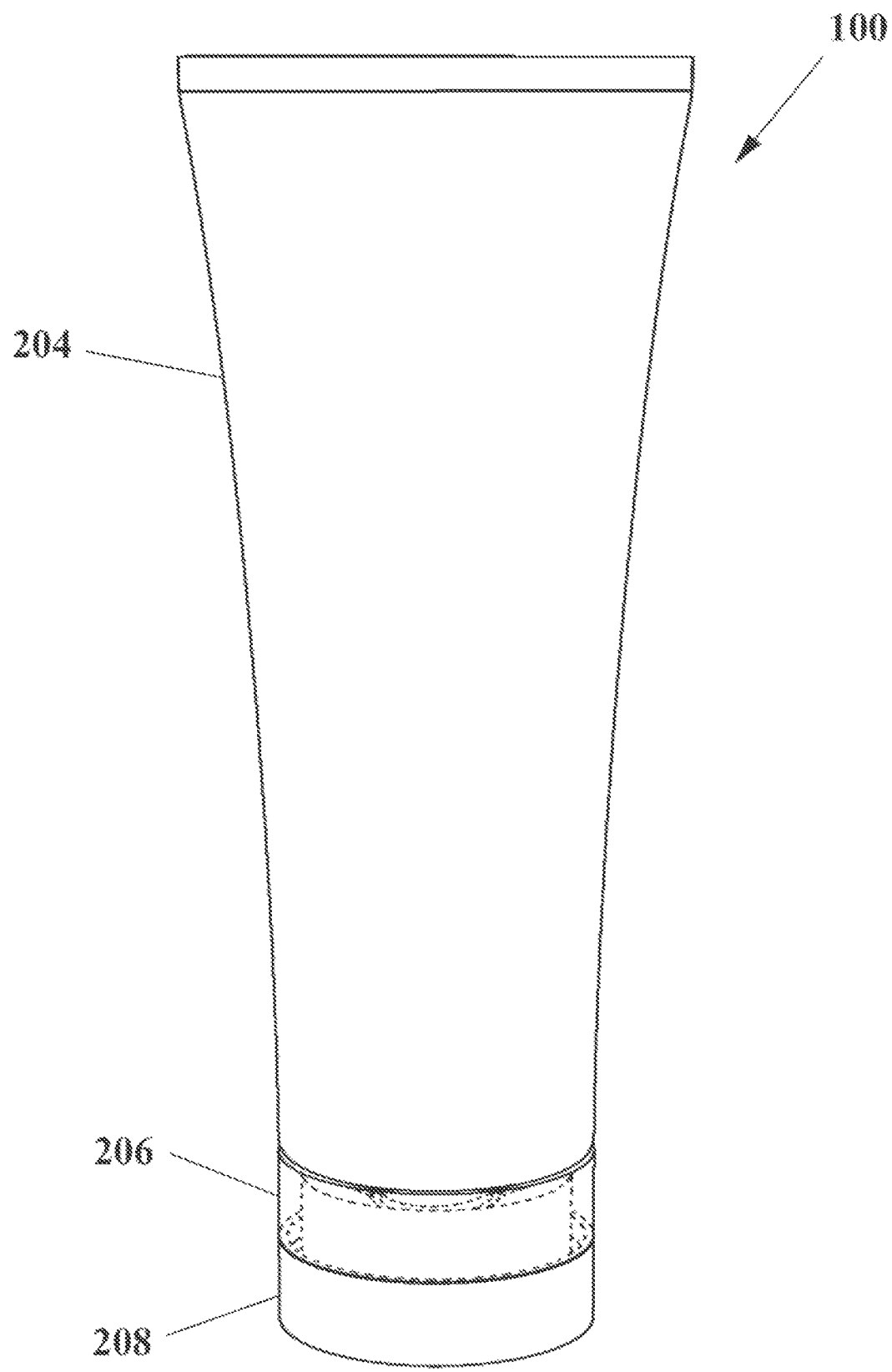
Figure 4:
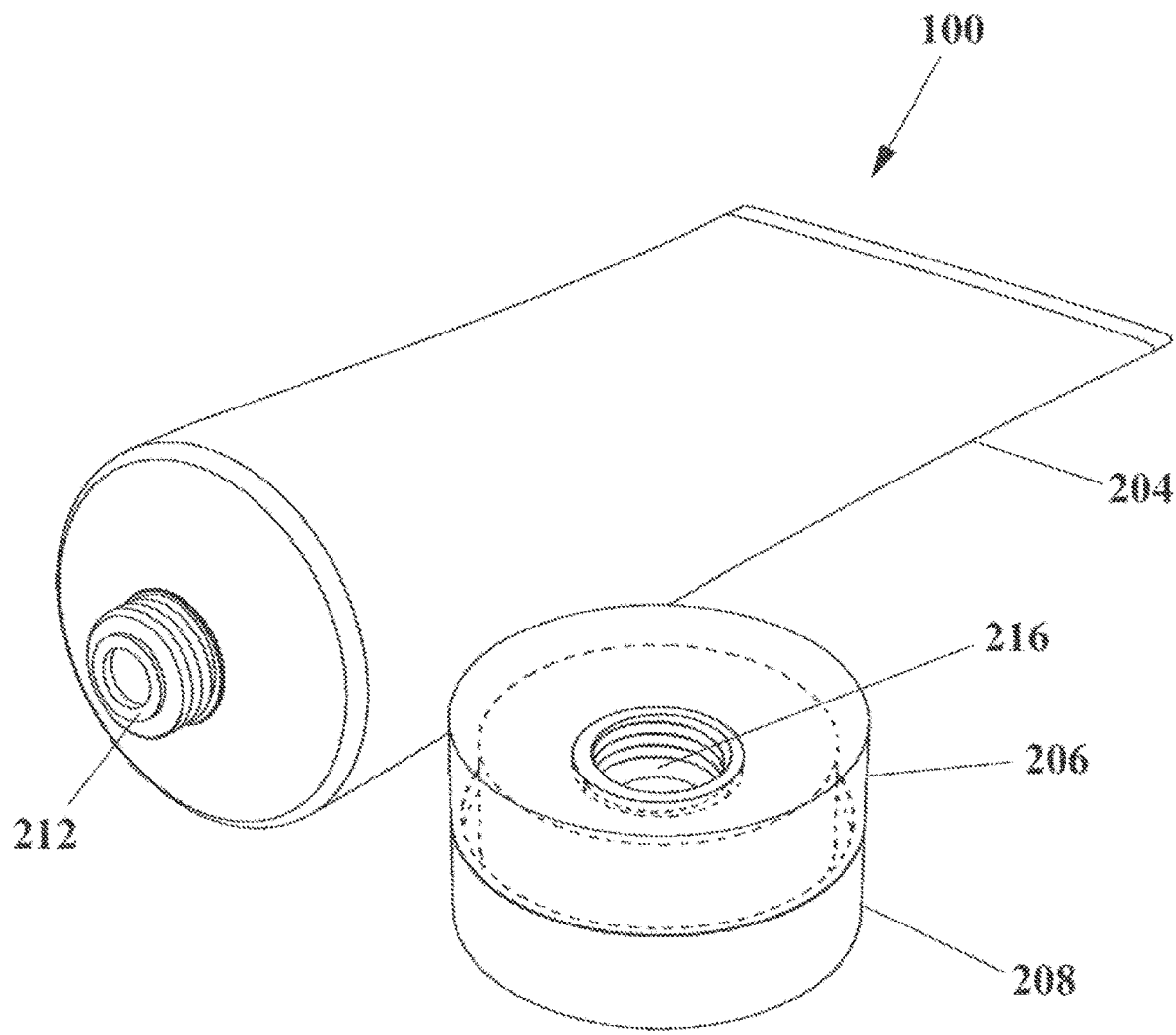

FIGS. 3 and 4 show a dispensing device 100 according to other embodiments of the present invention. In particular, the embodiments shown in FIGS. 3 and 4 include two containers 206, 204; hence it is a "dual container" dispensing device. The first container 206 can comprise and dispense (via the porous applicator 112) a first liquid dermatological agent and the second container can comprise and dispense a second dermatological agent that is the same as or, preferably, different from the first dermatological agent. The first container 206 is similar to the container 101 in FIGS. 1A-1C, but in the dual container configuration can also serve as a cap for the second container 204. The second container 204 can comprise a squeeze tube, for example. In that connection, the first container 206 may comprise a circular post which extends into the interior reservoir defined by the first container 206. The circular post may define a threaded recess 216 for receiving a corresponding threaded post 212 of the second container 204. The first container 206, therefore, can be removably attachable to the second container 204 by screwing the threaded post 212 of the second container 204 into the threaded recess 216 of the first container 206 (i.e. fully attached when fully threaded) and detachable by unscrewing the threaded post 212 from the threaded recess 216 (i.e. fully detached when fully unthreaded). The threaded recess 216 can comprise a top surface or cover that prevents the liquid from the second container 204 from flowing into the first container 206 when the first and second containers 206, 204 are coupled together in this manner. FIG. 3 show the first and second containers 206, 204 attached together while FIG. 4 shows the first and second containers 206, 204 detached separately (with the first container 206 upside down).

The first container 206 also comprises the porous applicator 112 and the dispensing device 100 can additionally comprise an overcap 208 that is similar to the cap 106 in the embodiments of FIGS. 1A-1C. The overcap 208 may be attached or coupled to the first container 206 via a suitable attachment means, as described above.

The first container 206 is preferably made of a hard, rigid, non-pliable material, such as a hard, rigid plastic, such as injection-molded, blow-molded, or extruded high-density polyethylene (HDPE). The first container 206 could also be made of glass. The first container 206 may be opaque or transparent. The second container 204 is preferably made from a pliable material, such as a pliable plastic, such as injection-molded, blow-molded, or extruded low-density polyethylene (LDPE), polypropylene, or polyethylene terephthalate glycol (PETG), for example.

Figure 5A:
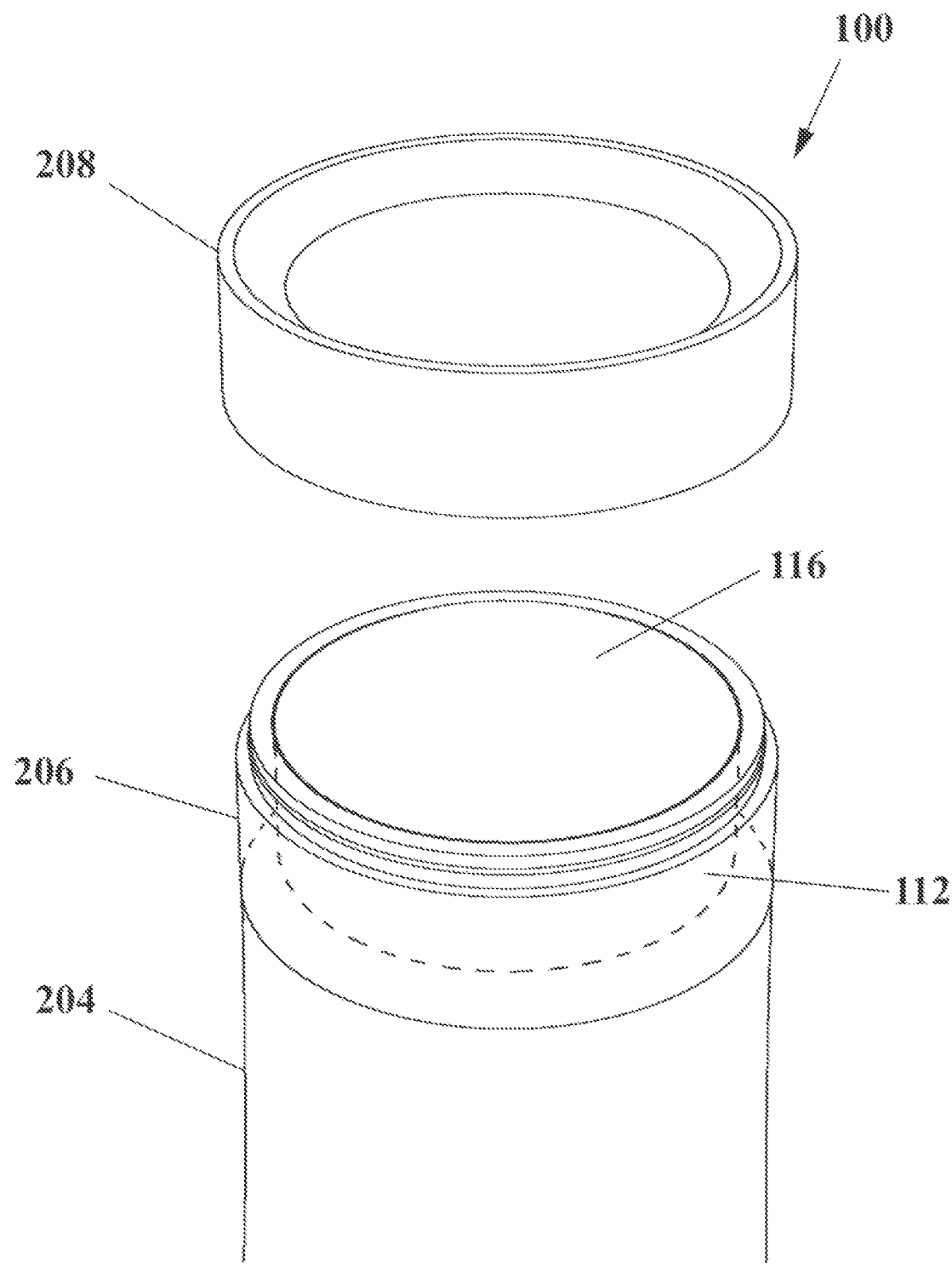
Figure 5B:
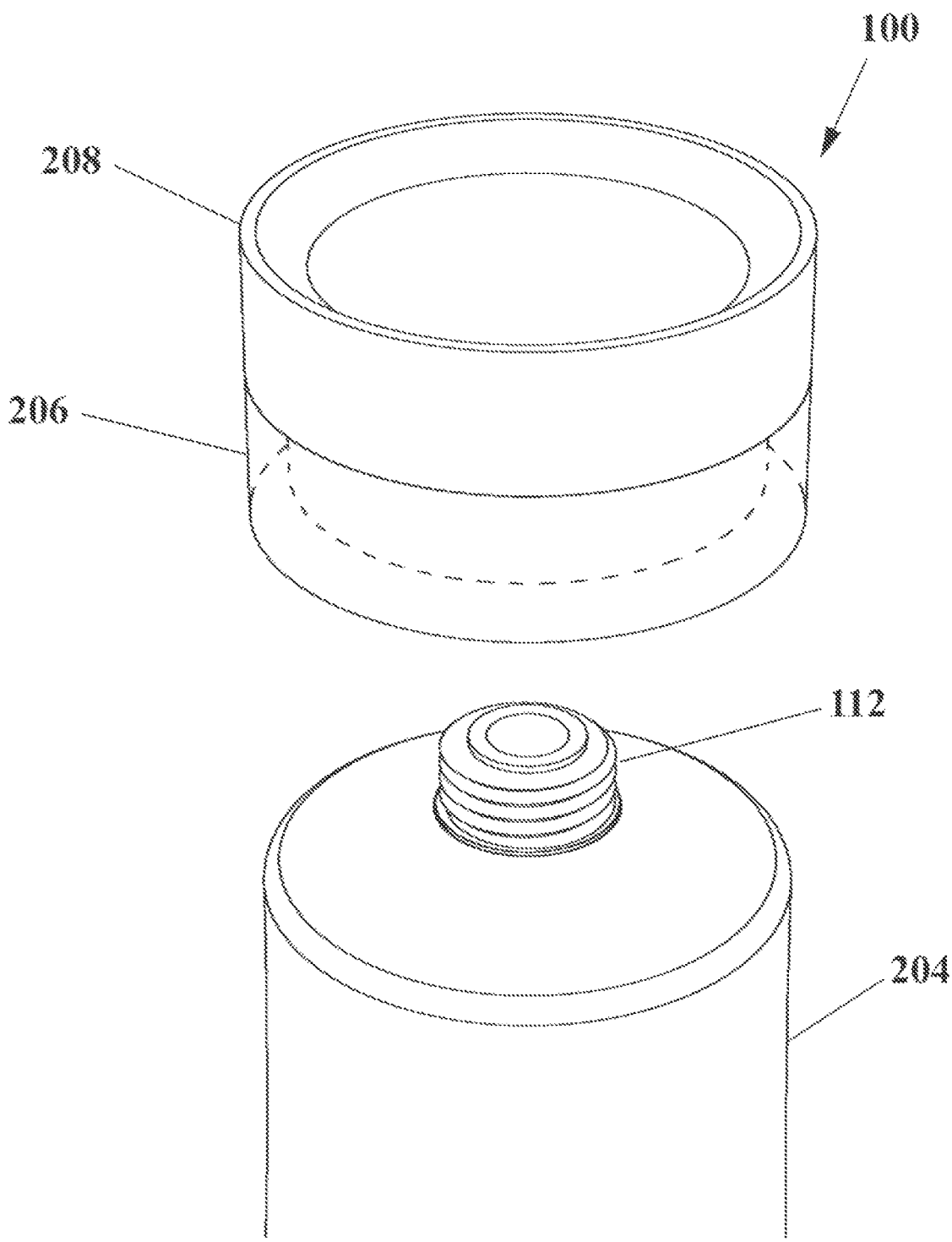

FIGS. 5A-5B are views of the dual configuration dispensing device 100 with components of the first container 206 detached from the second container 204 according to various embodiments of the present invention. FIG. 5A illustrates that the overcap 208 removed for application of the first liquid using the porous applicator 112. In one embodiment, the user may simply twist off the overcap 208 to detach it from the first container 206. Twisting off the overcap 208 enables the user to directly apply the first liquid using the porous applicator 112 with the advantage of reduction or prevention of leakage as discussed above. The porous applicator 112 is saturated such that the open celled pores of the porous applicator 112 absorb the first liquid in the first container 206, as described above.

The user may also twist off the entire first container 206 by unscrewing the threaded post 212 of the second container 204 from the threaded recess 216 of the first container 206. With the first and second containers 206, 204 detached, the user may apply a force to the second container 204 (e.g., squeeze it) to dispense the second liquid from an opening in the threaded post 212. Accordingly, there can be at least two different methods of dispensing the two liquids from the dispensing device 100, with at least one method for each of the two liquids, respectively.

Figure 6:
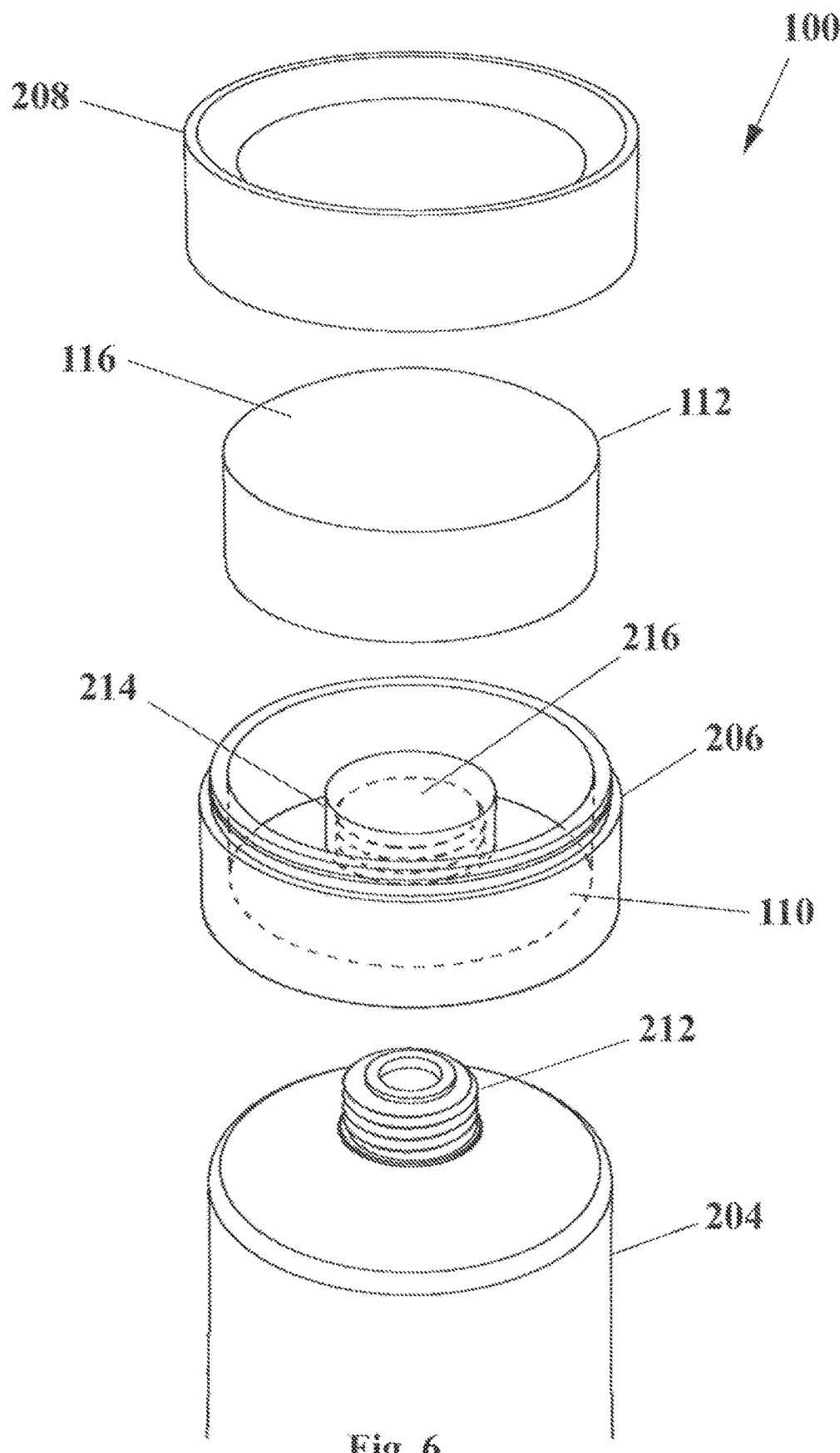

FIG. 6 is an exploded view of the dispensing device 100 positioned with the components of the first container 206 on top of the second container 204 according to various embodiments of the present invention. As shown in FIG. 6, the first container 206 may have a circular, internally-threaded post 214 that extend from the bottom surface of the first container 206 into the reservoir 110 defined by the first container 206. In various embodiments, the circular post 214 can comprise a downward-facing threaded recess 216 for receiving the corresponding threaded post 212 of the second container 204 for attachment and detachment of the first and second containers 206, 204. Although the circular post 214 of the first container 206 and the threaded post 212 of the second container 204 are both circular shaped, other suitable shapes are also possible. The porous applicator 112 may be shaped and sized to fit snugly into the reservoir 110 of the first container 206 so that the first liquid in the reservoir 110 can be wicked to the top surface 116 of the porous applicator 112 with reduced or prevented leakage of the first liquid from the first container 206. To that end, at least part of the porous applicator 112 may be hollow to accommodate the post 214 extending there into. Also, the post 214 may have top surface or cover at the top end of the recess to prevent the second liquid, in the second container 204, from being dispensed into the first container 206 when the two are connected.

Figure 7A:
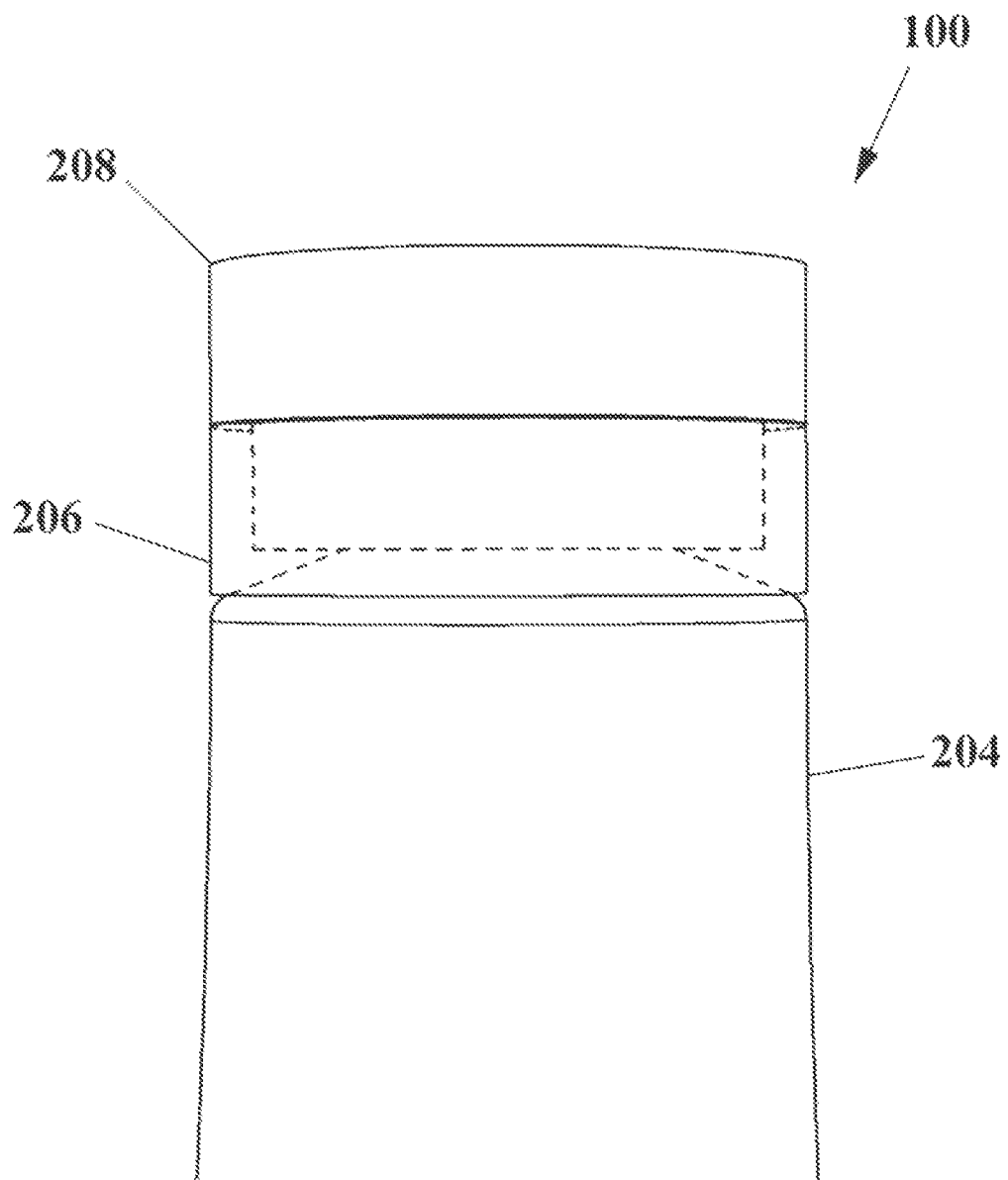
Figure 7B:
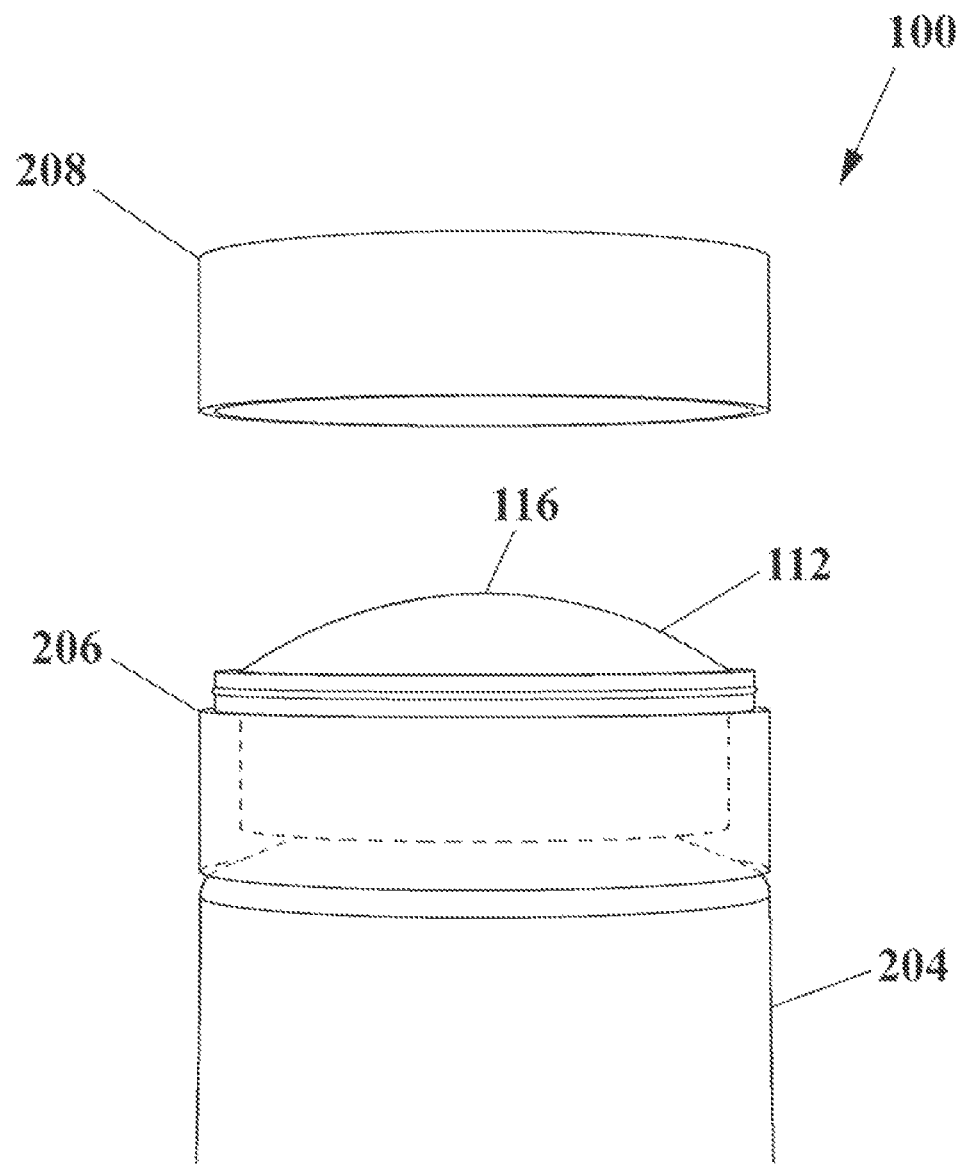
Figure 7C:
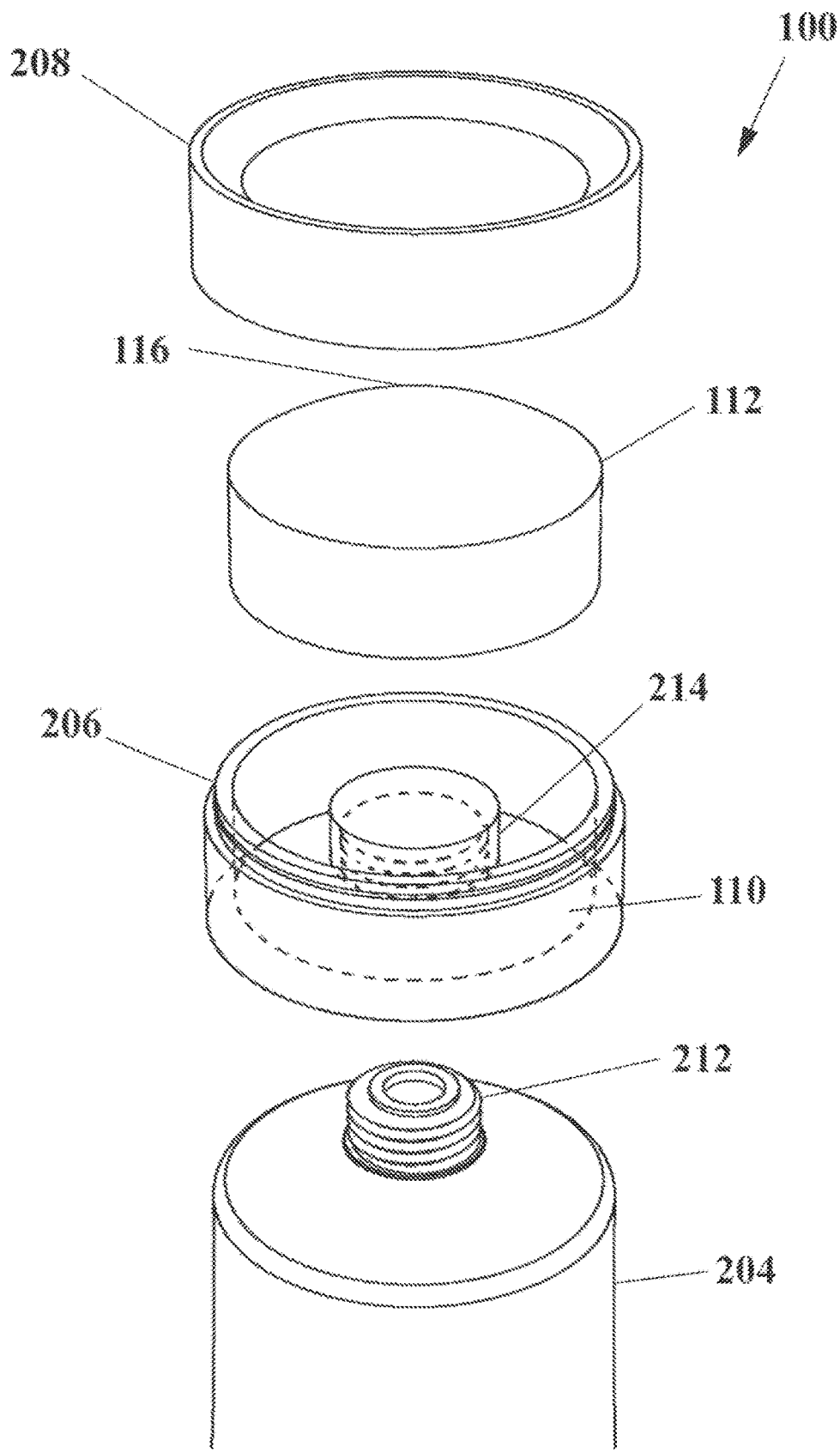

FIGS. 7A, 7B, 7C show additional views of the dual container dispensing device 100 according to various embodiments of the present invention. FIG. 7A shows the overcap 208 attached to the first container 206, with the first container 206 secured (threaded) to the second container 204. FIG. 7B shows the overcap 208 removed. And FIG. 7C is an exploded view showing the cap 208 detached, the porous applicator 112 out of the first container 206, and the first container 206 unthreaded from the second container 204.

Figure 8A:
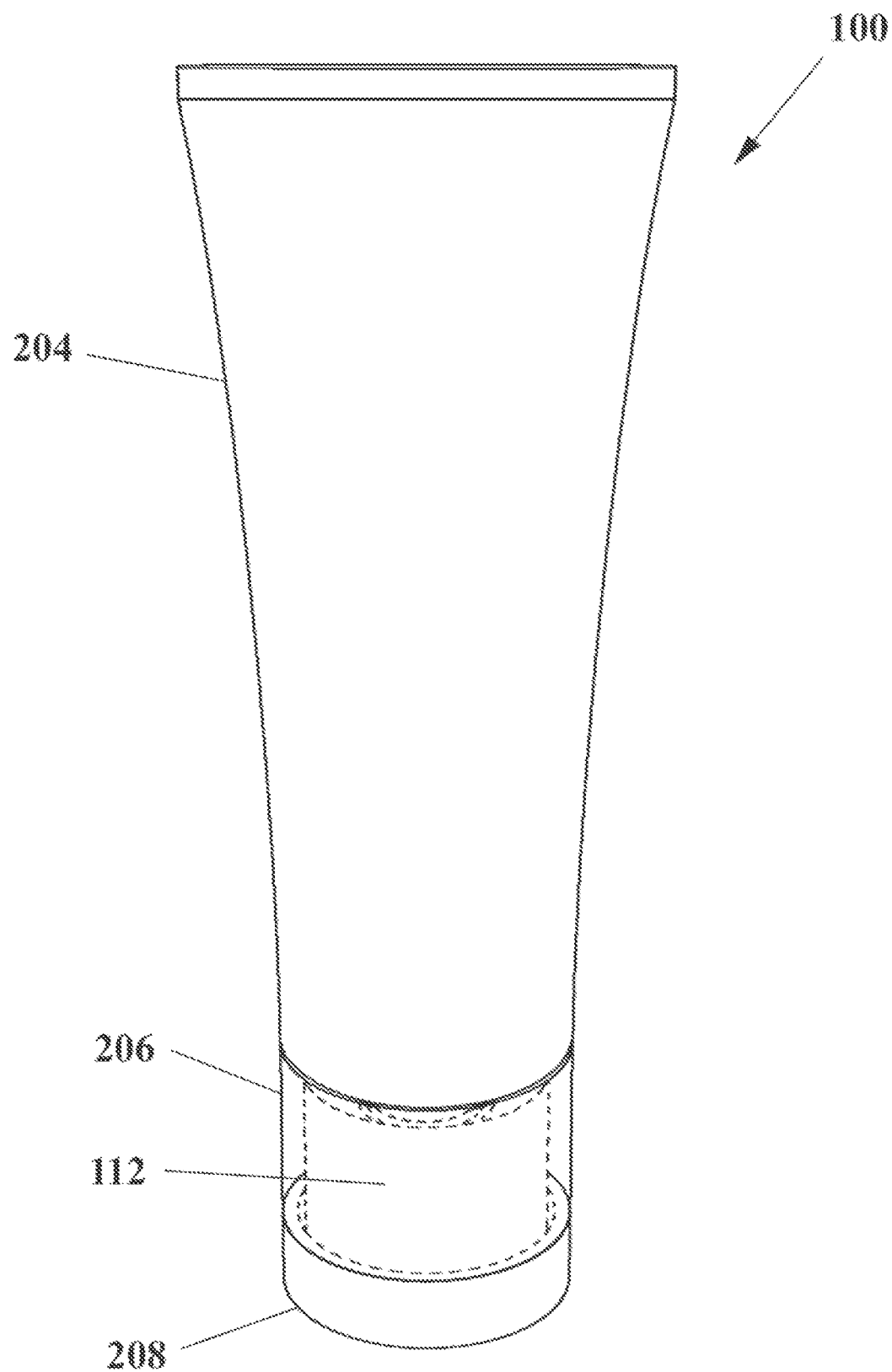
Figure 8B:
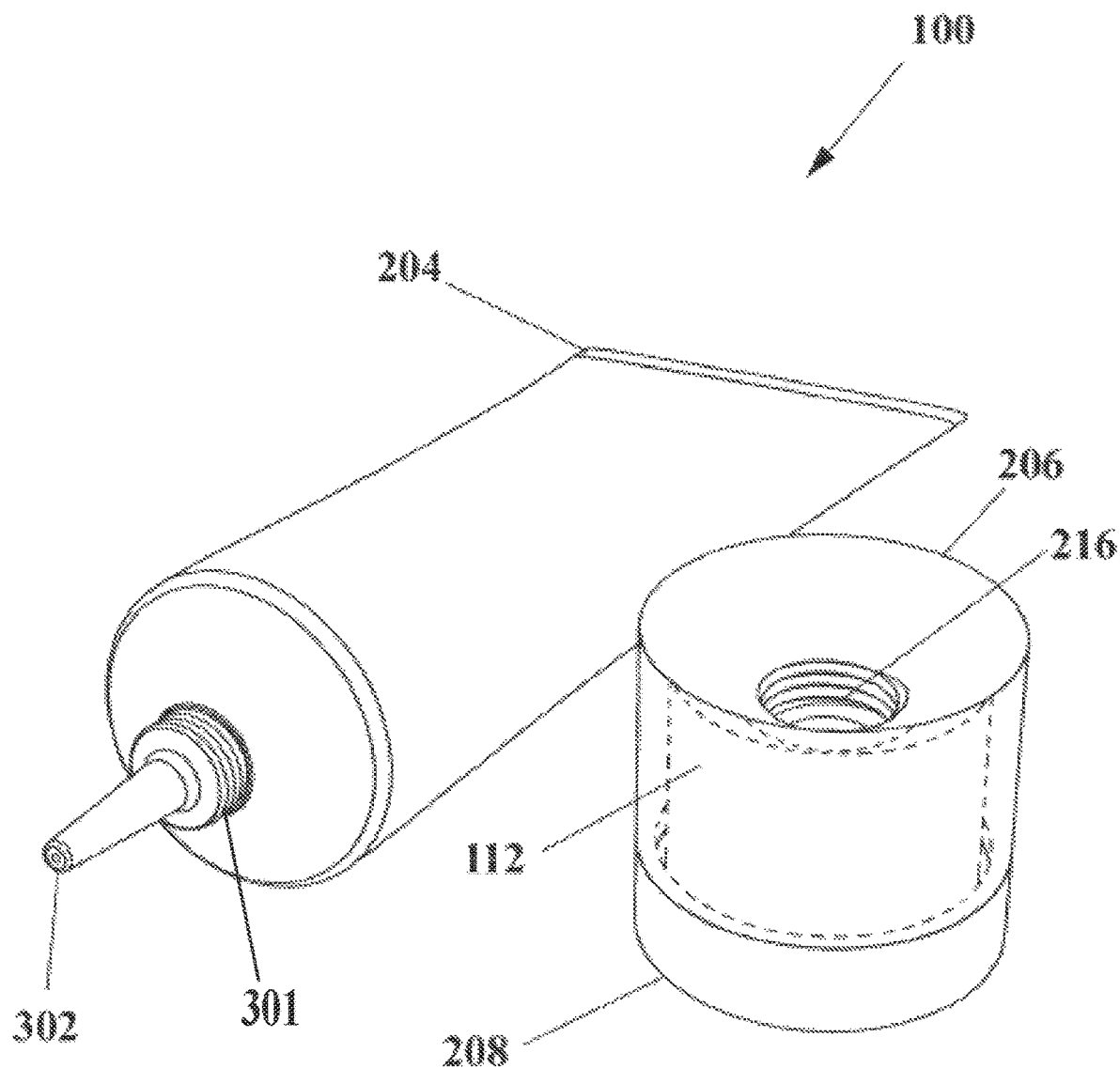
Figure 9A:
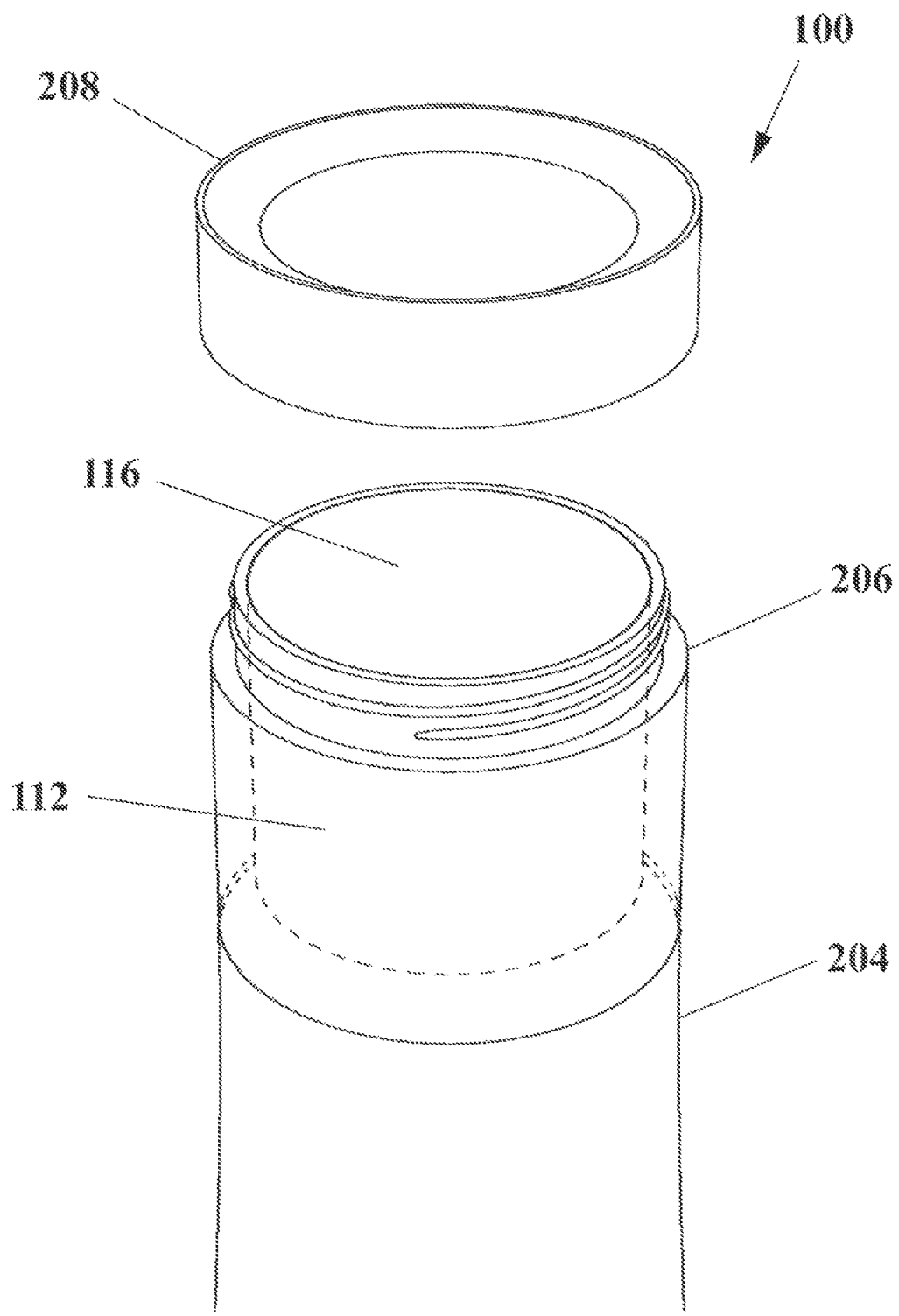
Figure 9B:
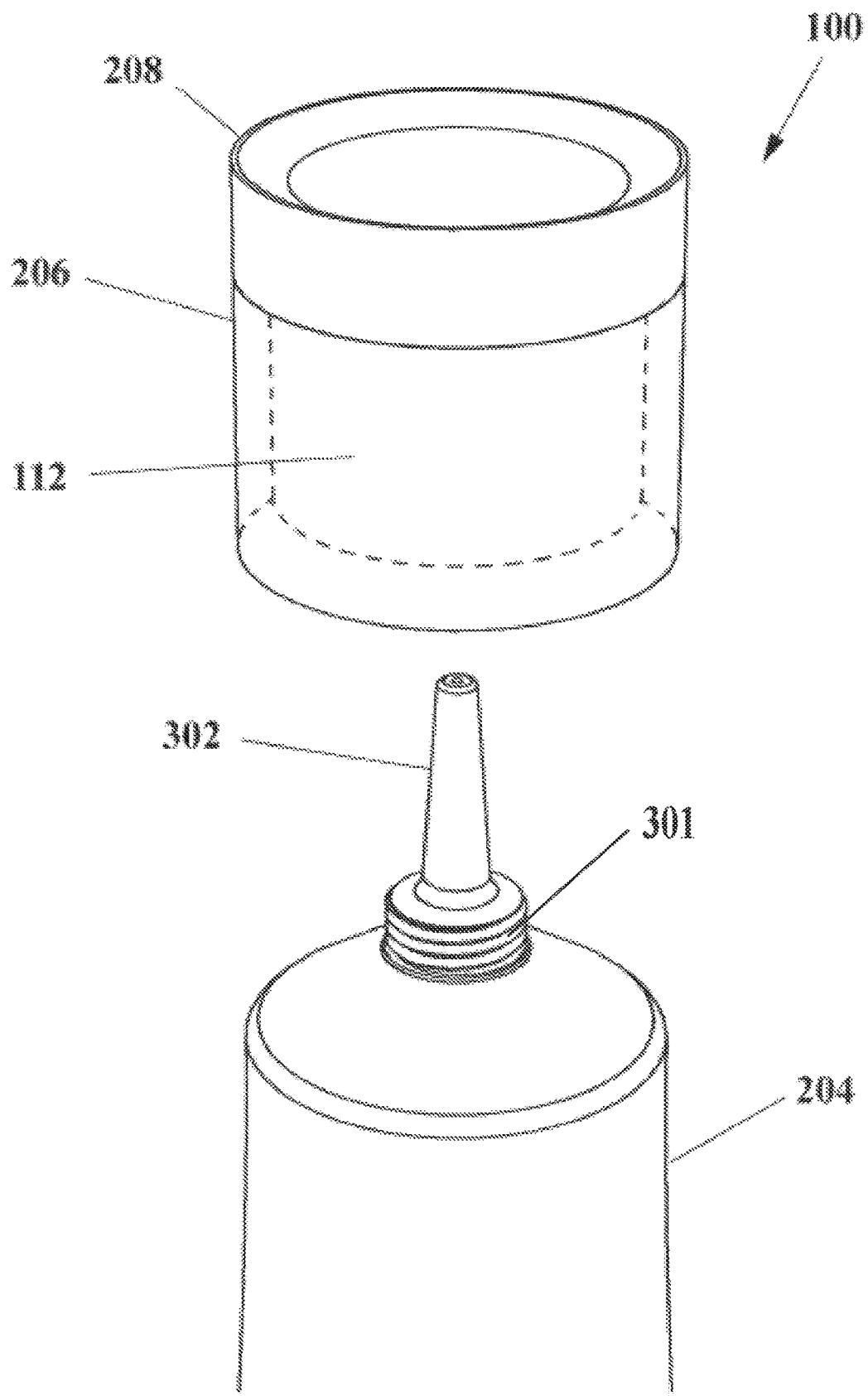
Figure 10A:
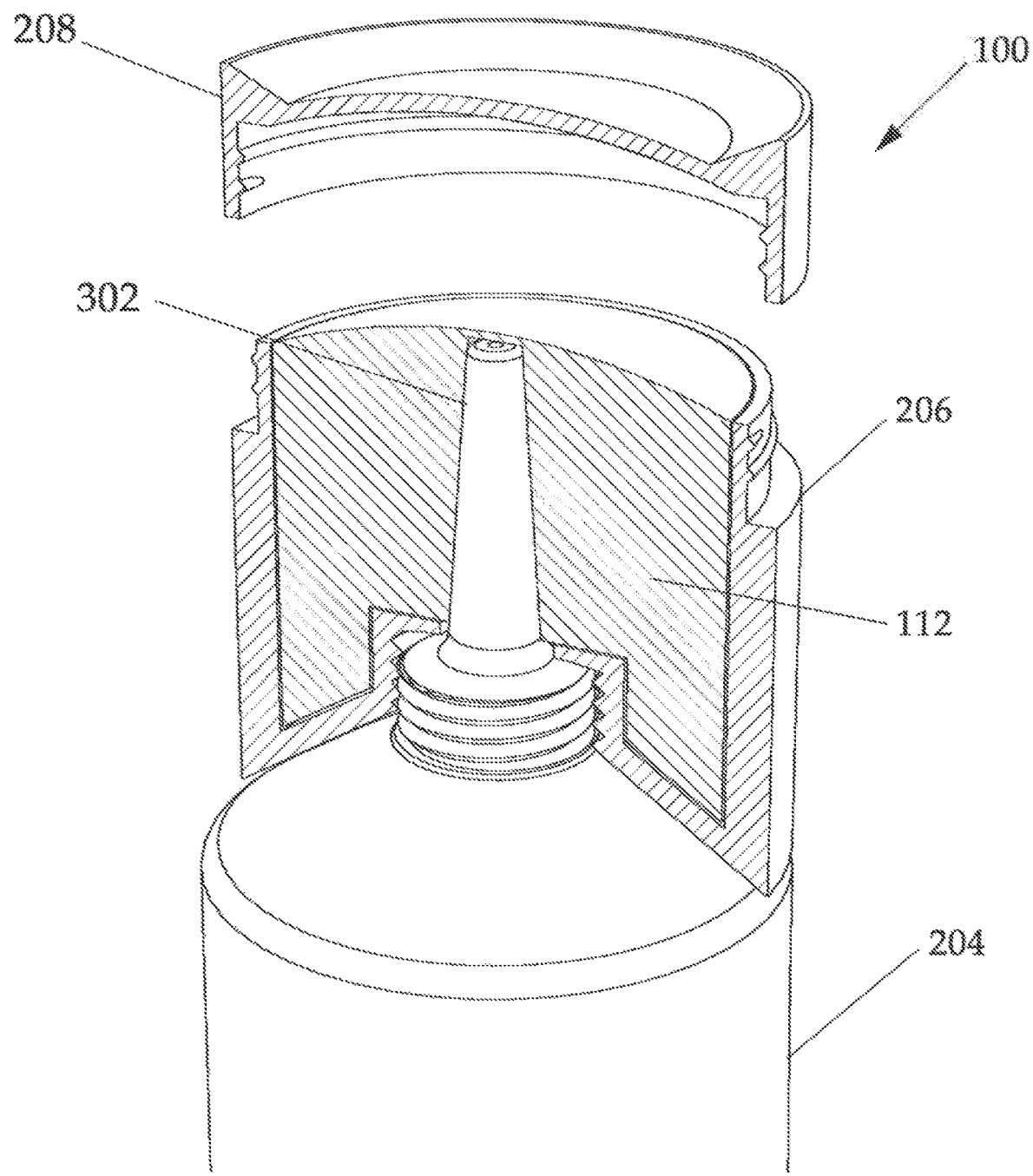
Figure 10B:
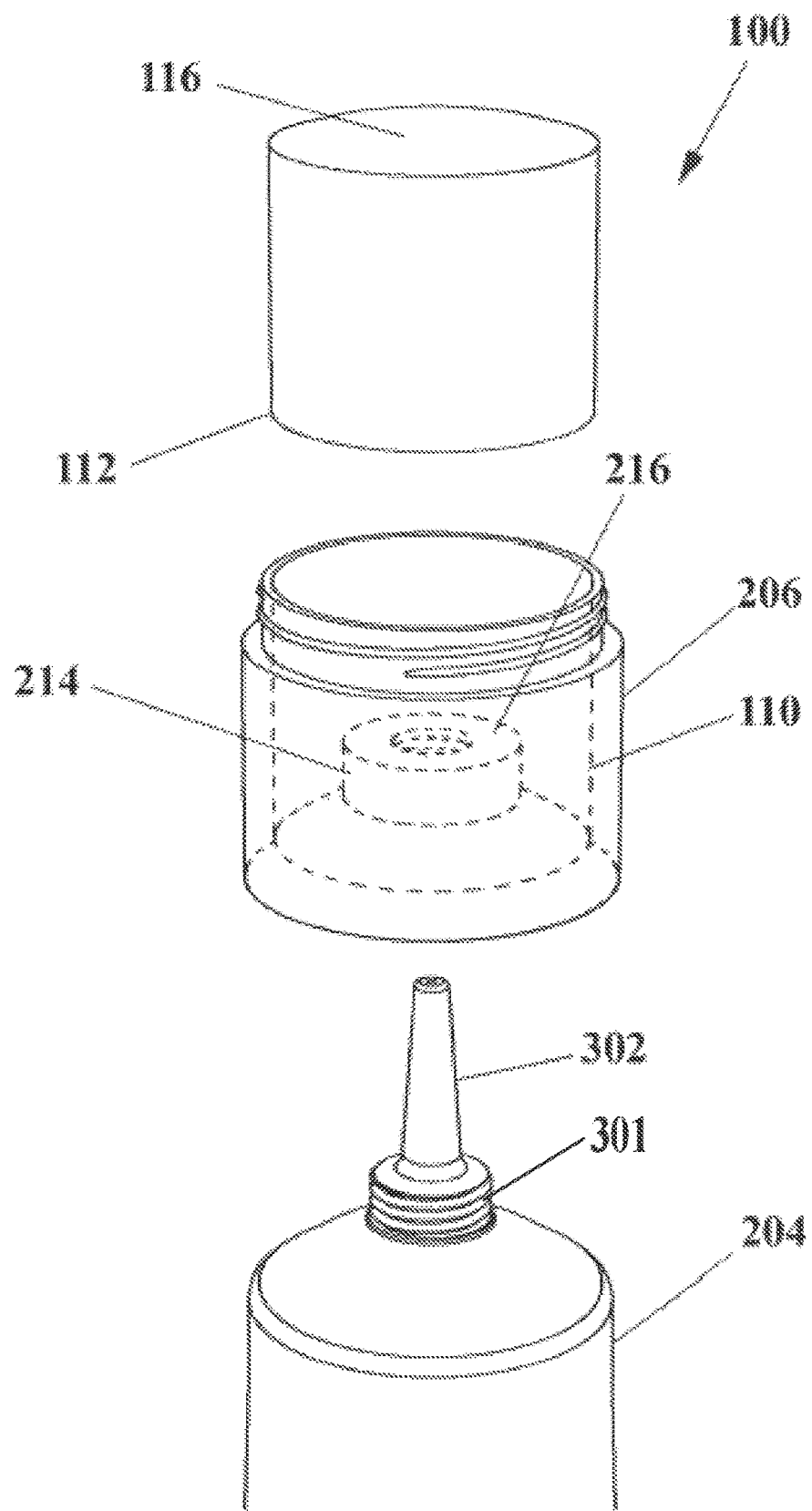

In other embodiments, as shown in FIGS. 8A-8B, instead of the threaded post 212 shown in FIG. 6, the second container 204 comprises an integrally-formed, elongated applicator tip 302 with a threaded portion 301 at the bottom thereof. The applicator tip 302 can extend into and through the threaded recess 216 of the first container 206 so that the threaded portion 301 of the applicator tip 302 is threaded to the threaded recess 216 of the first container 206. As such, in such an embodiment, the threaded post 216 of the first container 206 does not include the top cover, thereby allowing the top of the tip 302 to pass through the circular post 214 into the porous applicator 112. Because the applicator tip 302 is elongated, the first container 206 and the porous applicator 112 can be correspondingly elongated. The applicator tip 302 could be useful for applying the contents of the second container 204 at desired body locations. For example, the liquid dispensed by the first and/or second containers could be eye makeup remover.

FIGS. 9A-9B and 10A-10B are views of the dual configuration dispensing device 100 with the extended tip for the second (e.g., squeeze tube) container 204 according to various embodiments of the present invention. In this illustrated embodiment, the upper end of the tip does not reach the top surface 116 of the porous applicator 112 when the second container 204 is fully treaded to the first container. In use, therefore, the user can squeeze the second container to dispense the second liquid into the porous applicator 112, such that porous applicator 112 comprises both the first and second liquids, so that the user could simultaneously apply both liquids with the porous applicator 112. In this manner, the first and second liquids may be mixed together before dispensing via the porous applicator 112 to the desired area of application. For example, the second liquid could comprise a skin color or pigment agent that could be mixed with the first liquid to dispense a colored or pigmented first liquid. The user can apply just the first liquid by not squeezing the second container 204, and thereby not dispensing the second liquid into the porous applicator 112, although residual amounts of the second liquid could still be in the porous applicator 112 from a prior dispensing of the second liquid into the porous applicator. And the user could apply the second liquid, without the first liquid, by removing the first container 206 from the second container 204 and applying the second liquid via the tip 302 to the desired area with the first container 206 removed.

In other embodiments, as shown in FIGS. 11 and 12, the tip 302 could extend through to the top of the porous applicator 112. As such, the top surface of the porous applicator 112 can comprise an opening to which the tip 302 from the second container 204 extends. As such, the user can simultaneously apply the first and second liquids, but without mixing them prior to application, by simultaneously squeezing the second container 204, such that the second liquid is dispensed through the tip 302, and applying the first liquid with the porous applicator 112. FIG. 12 shows a cross section view of the porous applicator 112 and the overcap 208 according to various embodiments of the present invention. This figure shows that the overcap 208 can comprises a downward facing pintle 250 for plugging the opening in the tip 302 of the second container 204 when the first and second containers are connected and the overcap 208 is connected to the first container 206.

Figure 13A:
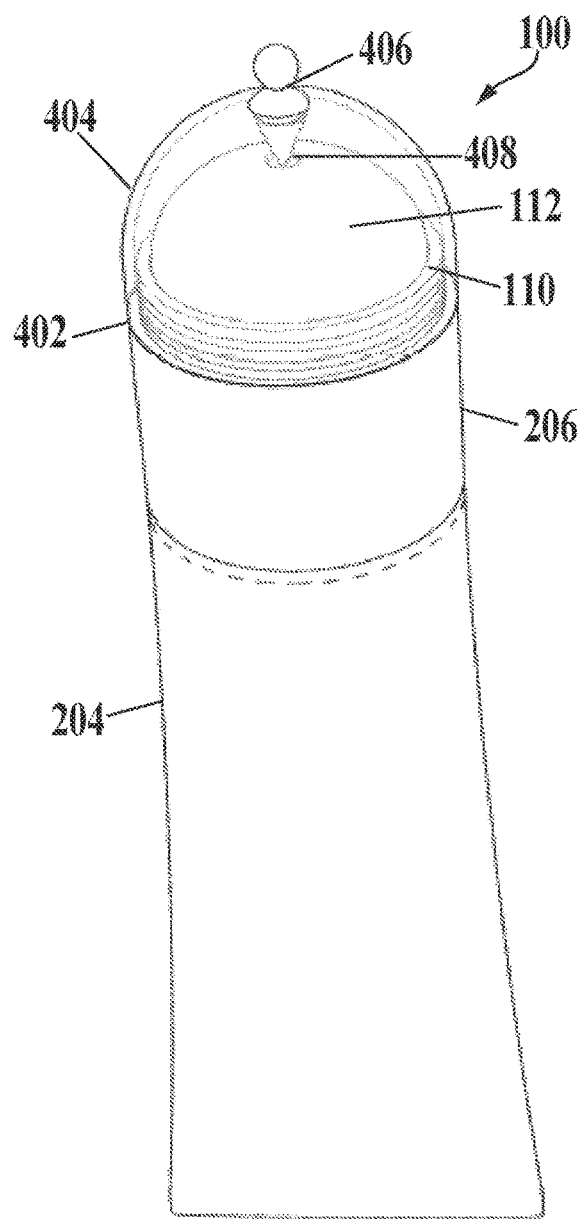
Figure 13B:
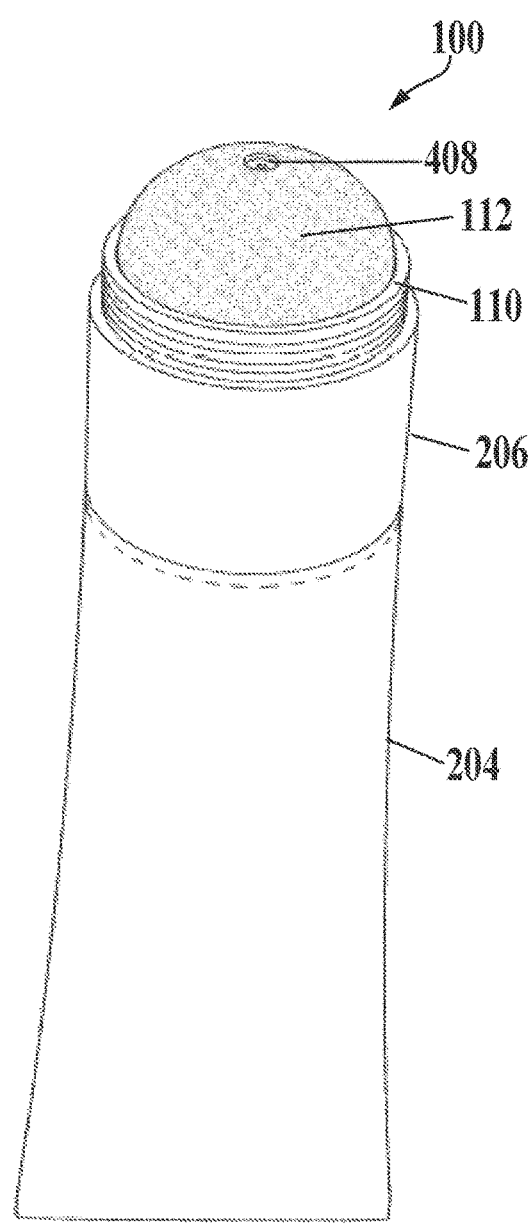
Figure 14:
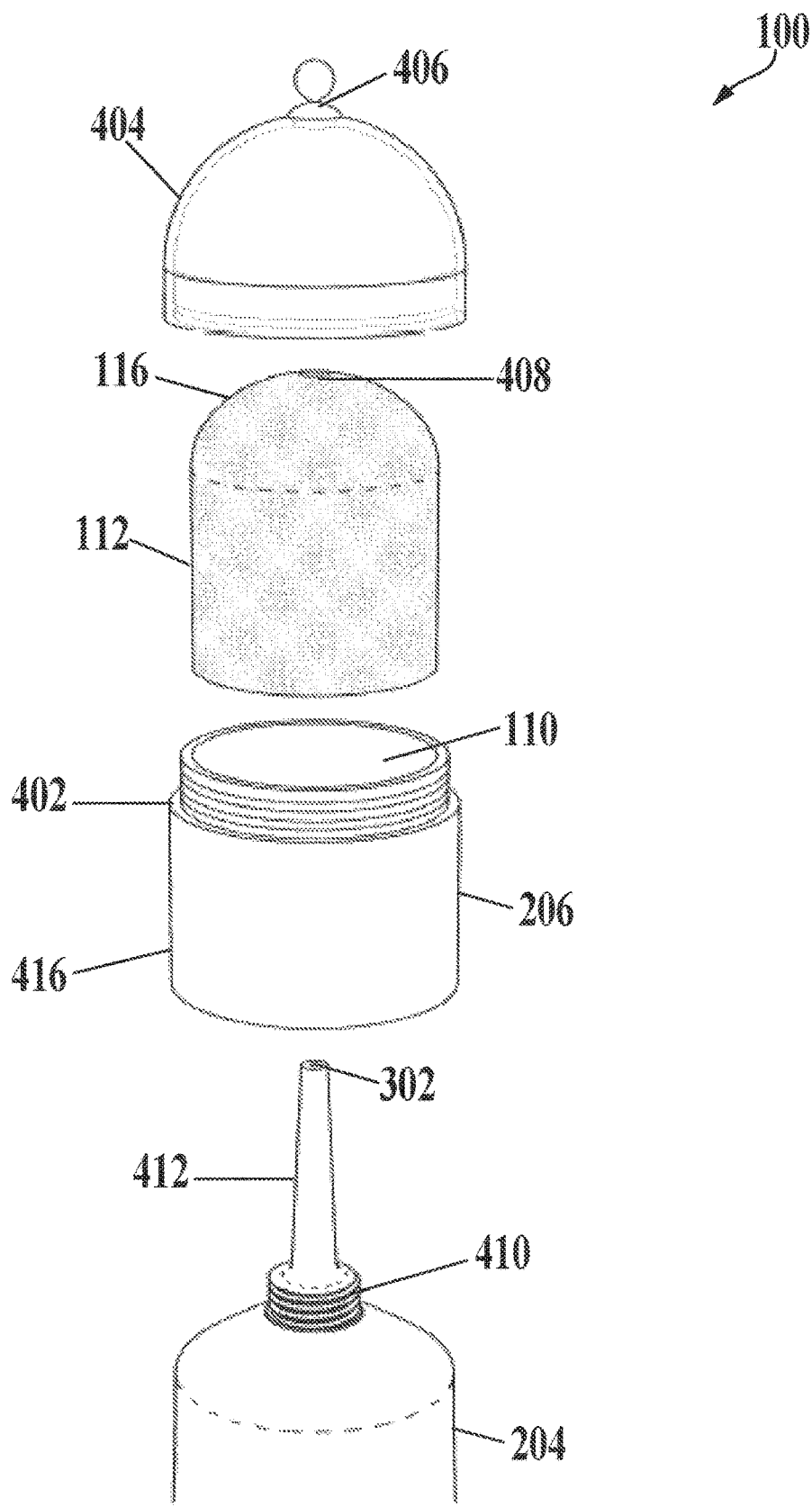

FIGS. 13A-B show an exterior view of a fountain configuration of the dispensing device 100 according to various embodiments of the present invention. In the fountain configuration, the dispensing device 100 is a "dual container" dispensing device that includes two containers 206, 204. As discussed above, a first liquid dermatological agent may be in the first container 206 while a second dermatological agent may be in the second container 204. Preferably, the second dermatological agent is a powder such as glitter or any other plurality of finely shaped particles produced by a grinding, crushing or other applicable disintegration process. However, other suitable cosmetic dermatological agents could possibly be used as the second dermatological agent. FIG. 14 shows an exploded view of the top of the fountain configuration dispensing device 100 shown in FIGS. 13A-B, and FIGS. 15A-B shows a cross-sectional view of the top of the fountain configuration dispensing device 100 according to various embodiments of the present invention. The first container 206 has a sidewall 416 (shown in FIG. 14) that defines the reservoir 110, in which the first dermatological agent and the porous applicator 112 reside.

The porous applicator 112 is a suitable porous material such as a sintered plastic that is inserted into the first container 206. Moreover, as described above, the porous applicator 112 dispenses the liquid dermatological agent in the first container 206 to the top surface of the porous applicator 112 via capillary action. The first container 206 may taper into a receding receiving portion 402 of the first container 206 for receiving a removably attachable overcap 404 (which functions similarly as the overcap 208). The receding receiving portion 402 thus can define a receiving edge on which the overcap 404 can attach snugly in a friction fit. FIG. 13A shows the overcap 404 attached to the first container 206 in this manner. The overcap 404 may comprise a pintle 406 (similar to pintle 250) which is designed to seal the applicator tip 302 (shown in FIG. 14) of the second container 204. In addition, the pintle 406 can be shaped to guide airflow for evenly distributing powder from the second container 204 over the porous applicator 112 surface. Other suitable means of uniformly distributing powder are also possible, as discussed below. Also, the pintle 406 may comprise an upper knob portion that a user may grasp to assist in detaching the overcap 404 from the first container 206. The user can similarly use the knob to attach the overcap 404 to the first container 206. In addition to its functional purpose, the pintle 406 may also be decorated according to a desired aesthetic purpose.

In this way, the overcap 404 is attachable and detachable to the first container 206 to shift between the closed and open positions of the dispensing device 100. The overcap 404 may have a transparent profile such that the sintered porous applicator 112 is visible even in the closed position. Having a clear (e.g., plastic) overcap 404 may be desirable for aesthetic and possibly functional purposes. For example, the transparent profile enables users to see the powder from the second container 204 dispense (e.g., flow, fountain, spray, sprinkle, or float onto the porous applicator 112) from the orifice 408. To this end, the applicator tip 302 of second container 204 has an opening and/or is connected to the orifice 408 in the porous applicator 112 so that the second dermatological agent is dispersed through the orifice 408 into the space between the top surface of the porous applicator 112 and the under surface of the overcap 404. As discussed above, the second container 204 can be a squeeze tube such that users may squeeze to force the powder therein out of the second container 204. More generally, the second container 204 may be a bottle or any suitable flexible package constructed from a pliable plastic, for example. The first and second containers 206, 204 may be removably attachable from each other as discussed in connection with FIGS. 3 and 4. Alternatively, the first and second containers 206, 204 can be manufactured integrally as one integrated dispensing device 100. That is, the first and second containers 206, 204 can be permanently attached as one comprehensive container.

FIG. 13B portrays the dispensing device 100 without the overcap 404 so that the porous applicator 112 is exposed. In this diagram, the top surface of the porous applicator 112 is coated with the dispersed powder from a prior squeezing of the second container 204. Preferably, the overcap 404 is closed while the powder is being dispensed through the orifice 408. The distribution of the powder can be used to create a "fountain" effect. In FIG. 13B, the porous applicator 112 has a domed shape resulting in a half spherical applicator surface. However, other shapes for the porous applicator 112 are also possible. These other shapes may be designed to perform specific tasks. For example, the top surface of the porous applicator 112 may be a flat surface for using the entire surface of the porous applicator 112 to evenly contact skin. Additionally, as shown in FIG. 13A, there is space between the overcap 404 and the porous applicator 112. This space could be useful for powder to flow and disperse onto the top surface of the porous applicator 112. Stated differently, the powder is dispersed about the space such that the dispensing appears to function similarly to that of a fountain. Also, more than one orifice 408 could be provided. The one or more orifices 408 could be located at other places besides the center. For example, the one or more orifices 408 could be off-center at a left or right portion of the porous applicator 112 surface.

Figures 15A, 15B:
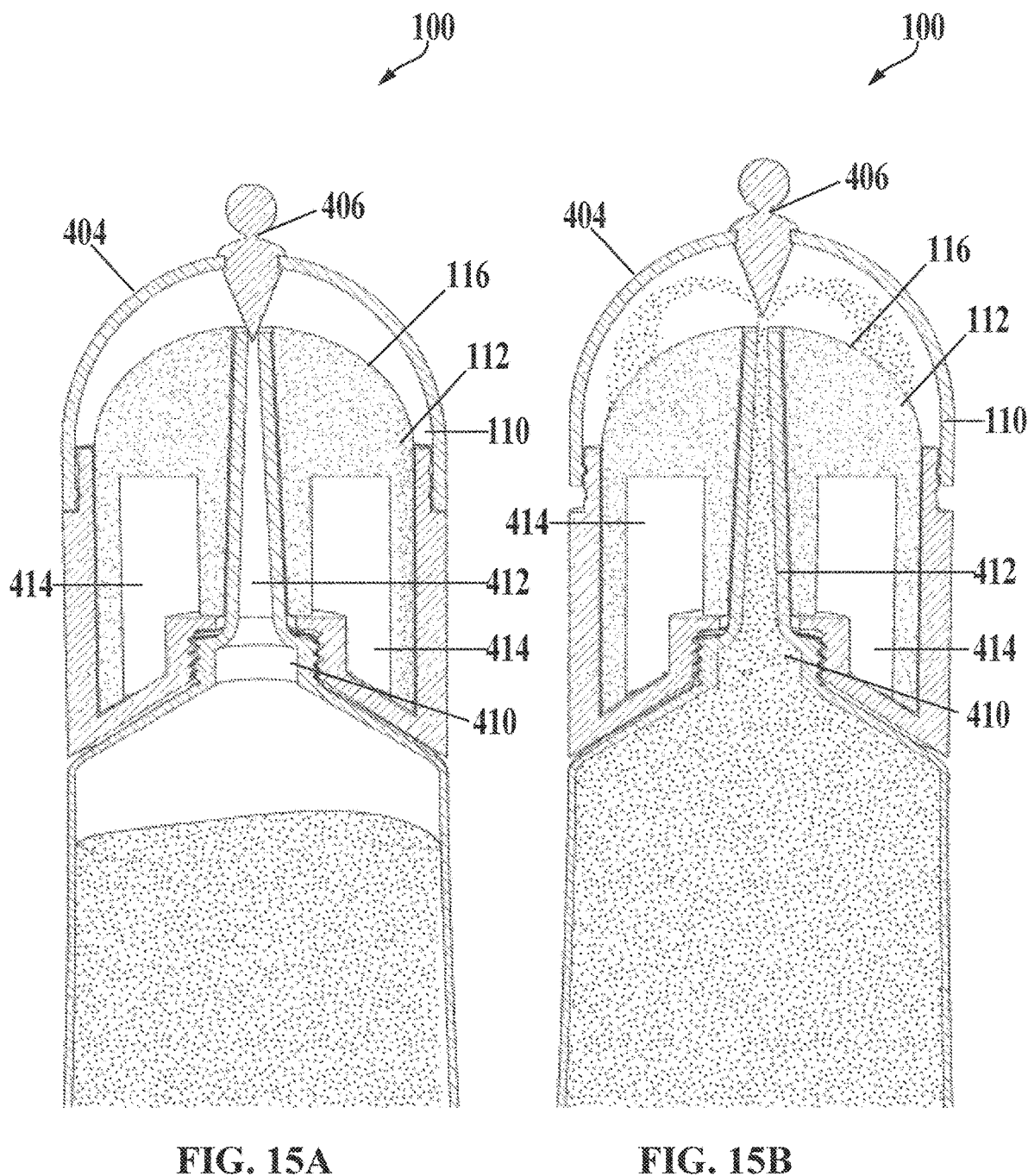

When the porous applicator 112 is coated with the powder, the user can simultaneously apply the first dermatological agent in the first container 206 (via the capillary action of the porous applicator 112) and the dispersed powder using the porous applicator 112 (e.g., by touching the porous applicator 112 to the user's skin). As shown in FIG. 14, the applicator tip 302 may have a threaded base portion 410 and a long nozzle 412. The first container 206 may form a closure base such that the first container 206 is threaded on a bottom surface to accept the applicator tip 302 and the rest of first container 206 is shaped on the top surface to hold the porous applicator 112. That is, the first container 206 may be hollow and threadedly recessed to accommodate the threaded base portion 410 of the second container 204. This structure is shown in FIGS. 15A-15B. Additionally, the interior of the receding receiving portion 402 defines the reservoir 110 that is shaped to hold the second container 204 snugly in a friction fit. The receiving portion 402 may be tapered relative to the annular sidewall 416. As shown in FIG. 14, the orifice 408 is a through-hole for the porous applicator 112.

FIGS. 15A-15B show cross sectional views of the fountain configuration dispensing device 100 with the pintle 406 in sealed and unsealed positions, respectively, according to various embodiments of the present invention. The pintle 406 transitions between the sealed and unsealed positions by moving the overcap 404 from a completely closed position (FIG. 15A) to a slightly open position (FIG. 15B) so that the pintle 406 is moved back from the top of the nozzle 412 and the orifice 408. In FIG. 15A, the overcap 404 is in the closed configuration causing the pintle 406 to seal the nozzle 412 of the second container 204. In this closed configuration, no (or very minimal) powder escapes from the nozzle 412, even if minor squeezing forces are inadvertently applied to the second container 204. When the pintle 406 is in the open configuration (FIG. 15B) and upon application of a squeezing force to the second container 204, the powder from the second container 204 is free to flow through the nozzle 412 of the applicator tip 302 and into the space between the top surface of the porous applicator 112 and the overcap 404, and to eventually settle onto to the top surface of the porous applicator 112. As such, a center portion of the porous applicator 112 may be hollow to accommodate the nozzle 112. The nozzle 412 prevents the first dermatological agent in the first container 204 (and the porous applicator 112) from mixing with the powder passing through the nozzle 12. In this way, the nozzle 412 defines a route to bypass the porous applicator 112. This may be advantageous because powder mixing with the first dermatological agent might cause clumping and poor dispensing performance of the dispensing device 100. The top end of the nozzle 412 terminates at the orifice 408, as shown in FIGS. 15A-15B.

Moreover, as shown in FIGS. 15A-B, the porous applicator 112 may define a void 414 under the porous applicator 112 to hold the first dermatological agent of the first container 206. In particular, a bottom portion of the porous applicator 112 may be cored out to create the cored portion 414. In other words, the space 414 is a hollow portion of the porous applicator 112 where the first dermatological agent is contained. FIG. 15A depicts the powder inside second container 204 in a non-active position. In contrast, FIG. 15B depicts the pintle 406 disengaged from the orifice 408 in the open configuration so that the powder can be dispensed. The pintle 406 can be shaped to guide the airflow from the orifice 408 to evenly divide and distribute the powder. The pintle 406 may work in conjunction with the overcap 404, whose domed upper surface can be helpful for evenly distributing the powder. Additionally or alternatively, one or more baffles, guides, or shields can be utilized to localize powder dispersal to a specific area of the porous applicator 102. Accordingly, the user can obtain a higher proportion of the powder to first dermatological agent when contacting the particular portion of the porous applicator 102 surface where the localized powder has collected. Additionally or alternatively, a dip tube or other suitable feed mechanism can be included in the dispensing device 100. The dip tube may be useful for precisely dispensing a small portion of the powder, the first dispensing agent, or a combination of both as described above.

Figure 16:
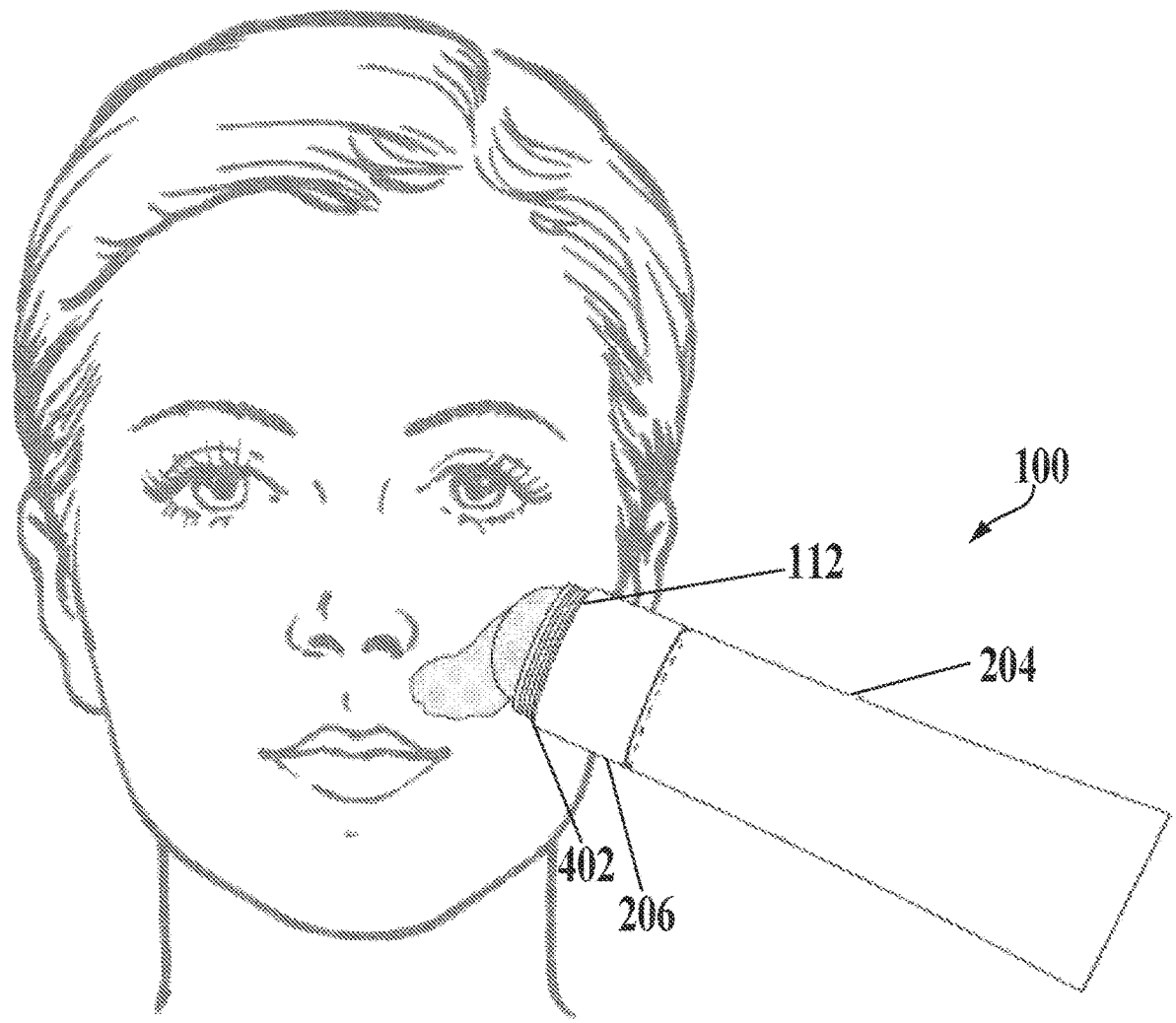

Although FIGS. 15A-15B show a two position overcap 406 mechanism, other suitable mechanisms or systems are also possible. For example, a rotary switch could be used to control powder dispensing from the flexible second container 204. Dispensing of the powder includes flowing, fountaining, spraying, sprinkling, or floating onto the porous applicator 112. In general, any configuration or system enabling powder to freely exit the second container 204 for dispensing as described above is contemplated. FIG. 16 shows the fountain configuration dispensing device 100 being used to simultaneously apply the powder and the liquid dermatological agent to a user's skin, according to various embodiments of the present invention. It should be noted, however, that the dispensing device 100 can be used to dispense the first dermatological agent with or without the powder.

Figure 17A:
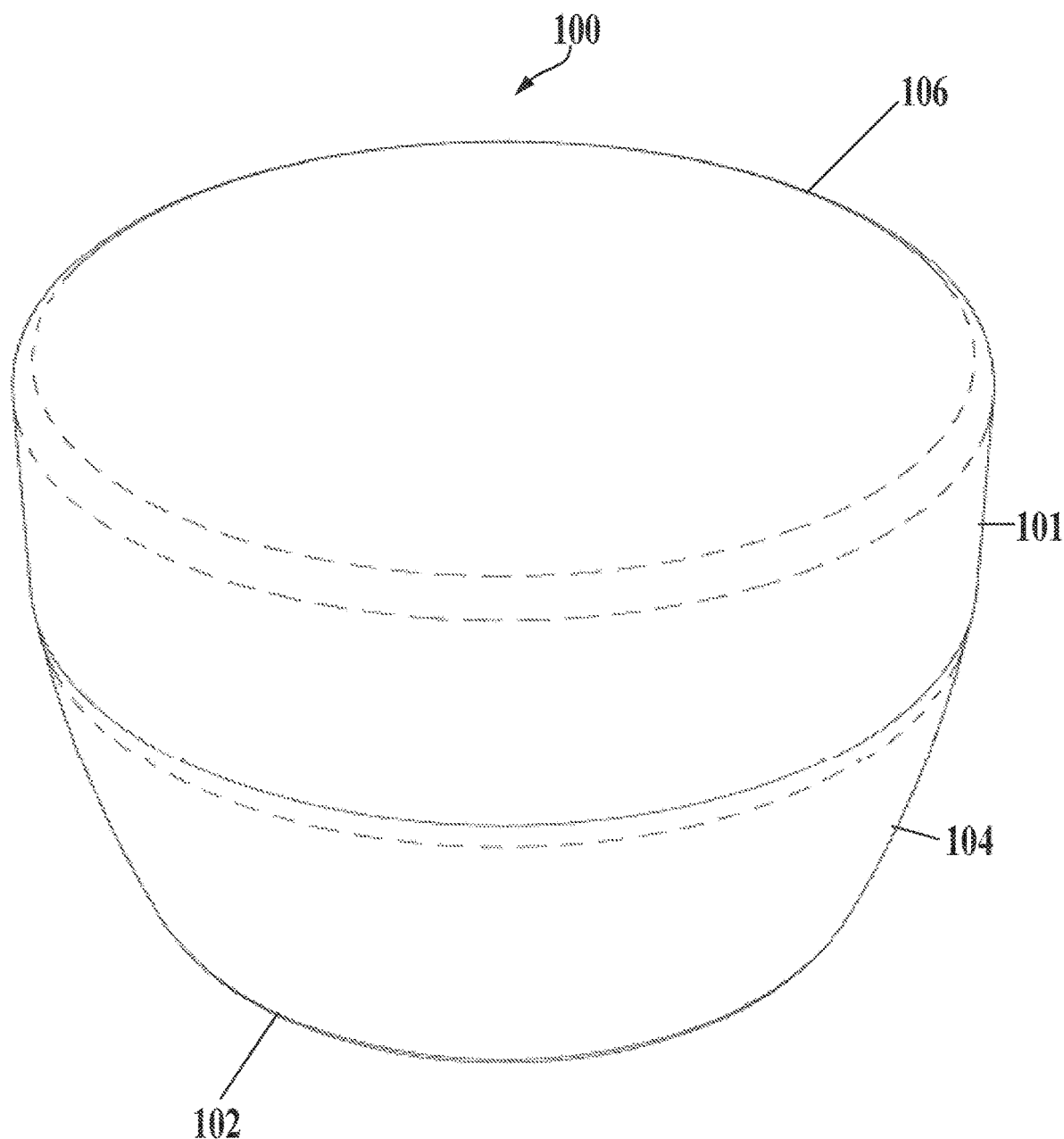
Figure 17B:
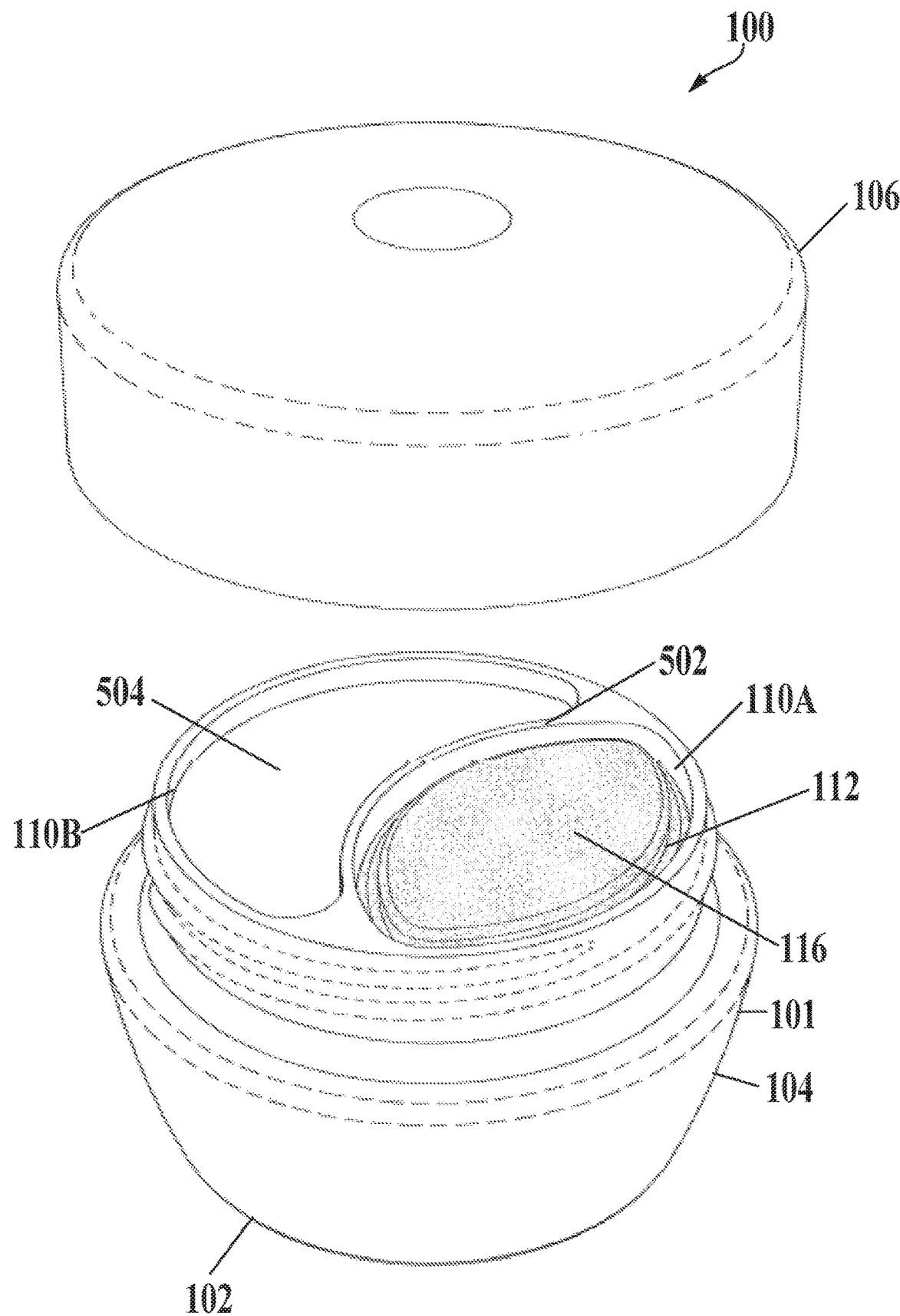

FIGS. 17A-B shows an interior wall configuration of the dispensing device 100 according to various embodiments of the present invention. As depicted in FIGS. 17A-B, the dispensing device 100 comprises a container 101 having a bottom surface 102, an annular sidewall 104, cap 106, and one or more interior walls 502 which collectively define one or more reservoirs 110. For example, as shown in FIGS. 17A-B, the container 101 may have one interior wall 502 defining two (first and a second) reservoirs 110, although the container 101 may have more than one interior wall 502, and thereby define additional reservoirs 110, as appropriate and/or desired. Dermatological agents (which may be liquids, such as creams or oils) may be in each reservoir and the porous applicator 112 may be held within at least one of the reservoirs 110, depending on the product's design. FIG. 17A depicts the cap 106 attached to the container 101 in a closed configuration, while FIG. 17B depicts the cap detached in an open configuration.

The wells or reservoirs 110 of the container 101 can be seen in FIG. 17B. As shown in FIG. 17B, the interior wall 502 forms a boundary between the wells (the first and the second reservoirs 110A-B). In the interior wall configuration, the porous applicator 112 may be placed in the first reservoir 110A while a cosmetic emulsion 504 such as a cream or lotion may be placed in the second reservoir 110B. FIG. 17B portrays the porous applicator 112 in the first reservoir 110A located on the right portion of the container 101, while the cosmetic emulsion 504 is in the second reservoir 110B located on the left portion. As discussed above, the porous applicator 112 may be used for dispensing a liquid dermatological agent such a serum through capillary action from the bottom of the first reservoir 110 to the top surface 116 of the porous applicator 112. Thus, the interior wall configuration of the dispensing device 100 results in at least a dual product system. That is, the first reservoir 110A contains a first cosmetic product saturated in the porous applicator 112 and the second reservoir 110B contains a second cosmetic product such as cosmetic cream 504.

Figure 18:
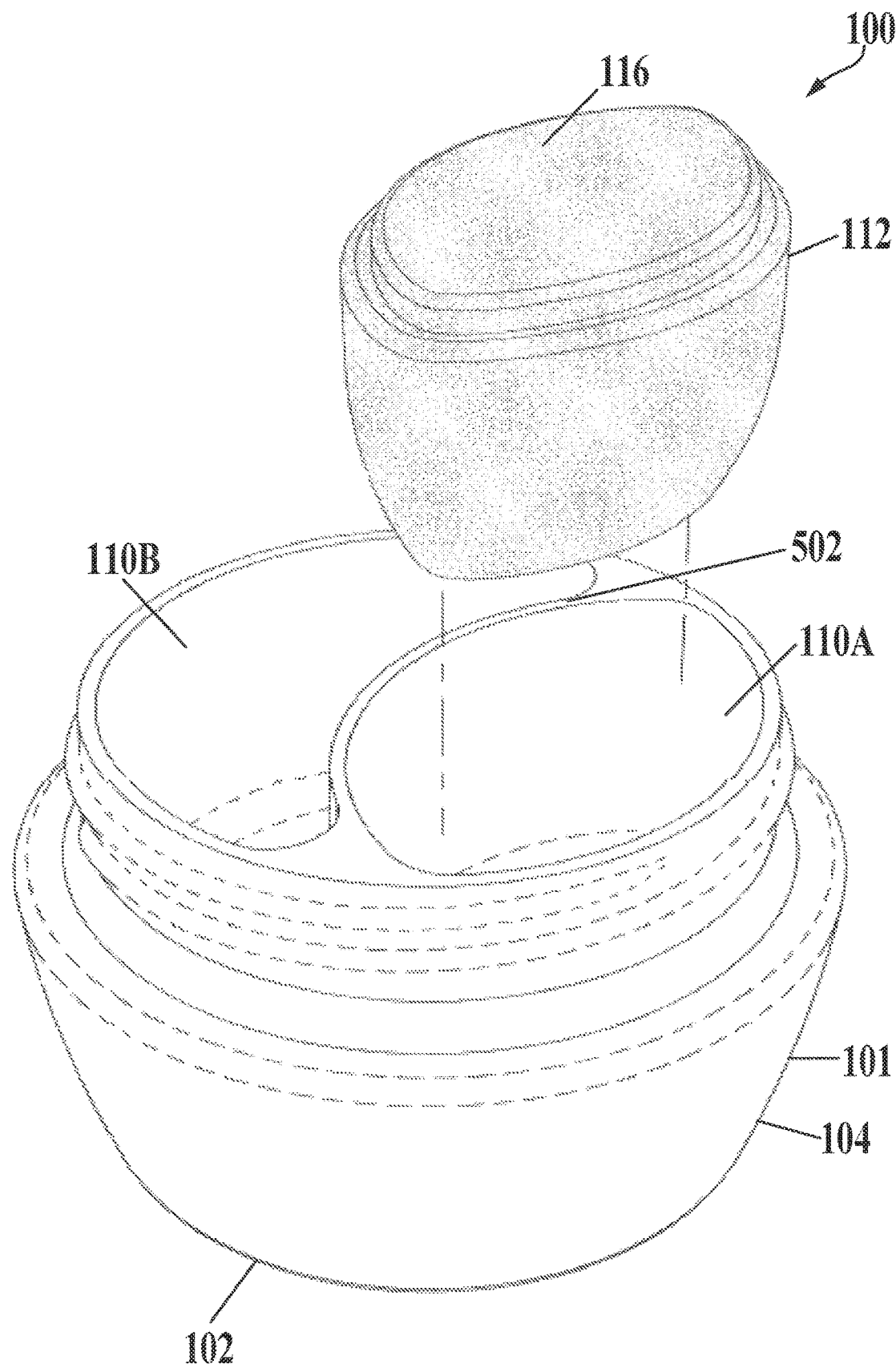

The cap 106 of the dispensing device 100 is removably coupled to the container 101. In other words, the cap 106 can be threaded or screwed onto the container 101. Similarly, cap 106 can be detached from the container 101 by being threaded or screwed off with a rotating motion. Alternatively, the cap 106 could be coupled to the container 101 based on a snug friction fit or other suitable means of attachment. Decoupling may occur using the same means. As illustrated in FIG. 17B, the container 101 may have a tapering threaded portion which acts as a receiving portion for the corresponding threaded interior portion of the cap 106 when the cap 106 is being screwed on or off. The porous applicator 112 also could be threaded in a tapered manner, as depicted in FIGS. 17B and 18. Although FIG. 17B shows the porous applicator 112 in the first reservoir 110A and the cream 404 in the second reservoir 110B, other dermatological agents or dispensing mechanisms can be placed in the reservoirs 110. For example, a second porous applicator 112 could be placed in the second reservoir 110B as well.

FIG. 18 is a view of the porous applicator 112 being inserted into the first reservoir 110 according to various embodiments of the present invention. The porous applicator 112 can be a textured part that is constructed as a sintered plastic part via a suitable sintering process, such as solid state sintering, liquid phase sintering or viscous sintering. The upper surface 116 of the porous applicator 112 may also define a dome for controlling a dosage of liquid dermatological agent dispensed by the dispensing device 100 through the porous applicator 112. Alternatively, the porous applicator 112 may define a recess in its upper surface 116 for dosage control in a similar manner as the protruding dome. The dome may be sized according to a standard dosage of the liquid dermatological agent so that when the user contacts the porous applicator 112 (e.g., with their finger), a controlled standard amount of liquid dermatological agent is dispensed onto the user's finger per contact. The porous applicator 112 may also define one or more trough areas for a greater amount of dermatological agent than that of the standard dosage to be dispensed per contact. For example, the trough areas could enable a dispensing amount equivalent to the user's fingertip. The dome and trough areas may be located on the top surface 116 of the porous applicator 112. Additionally, the dome, trough areas, or other parts of the porous applicator 112 may have unique textures or branding for aesthetic or advertising purposes. Any suitable textures and geometries may be created as part of the process for manufacturing the porous applicator 112. In the view of FIG. 18, the second reservoir 110 is empty.

Figure 19:
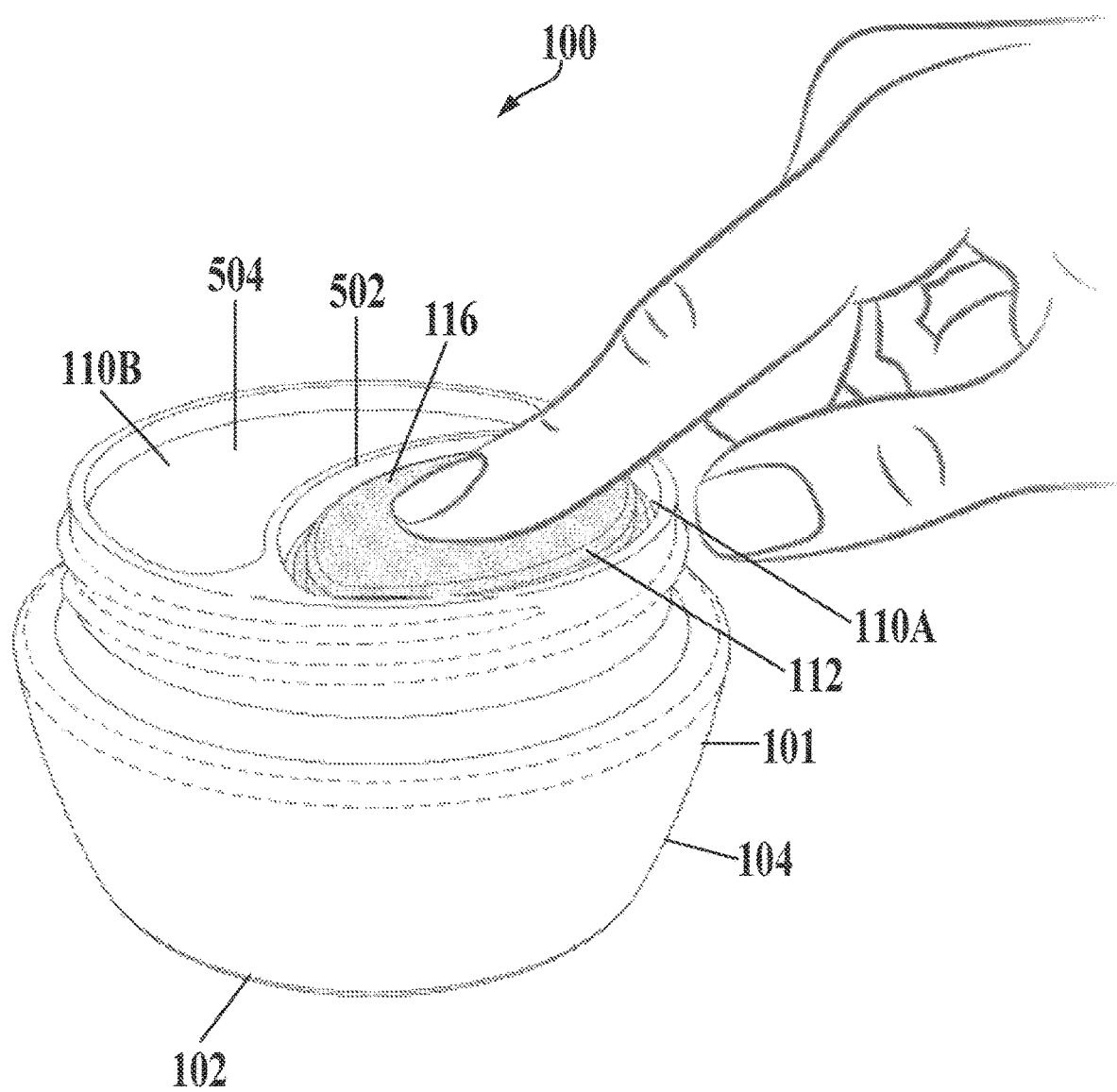
Figure 20:
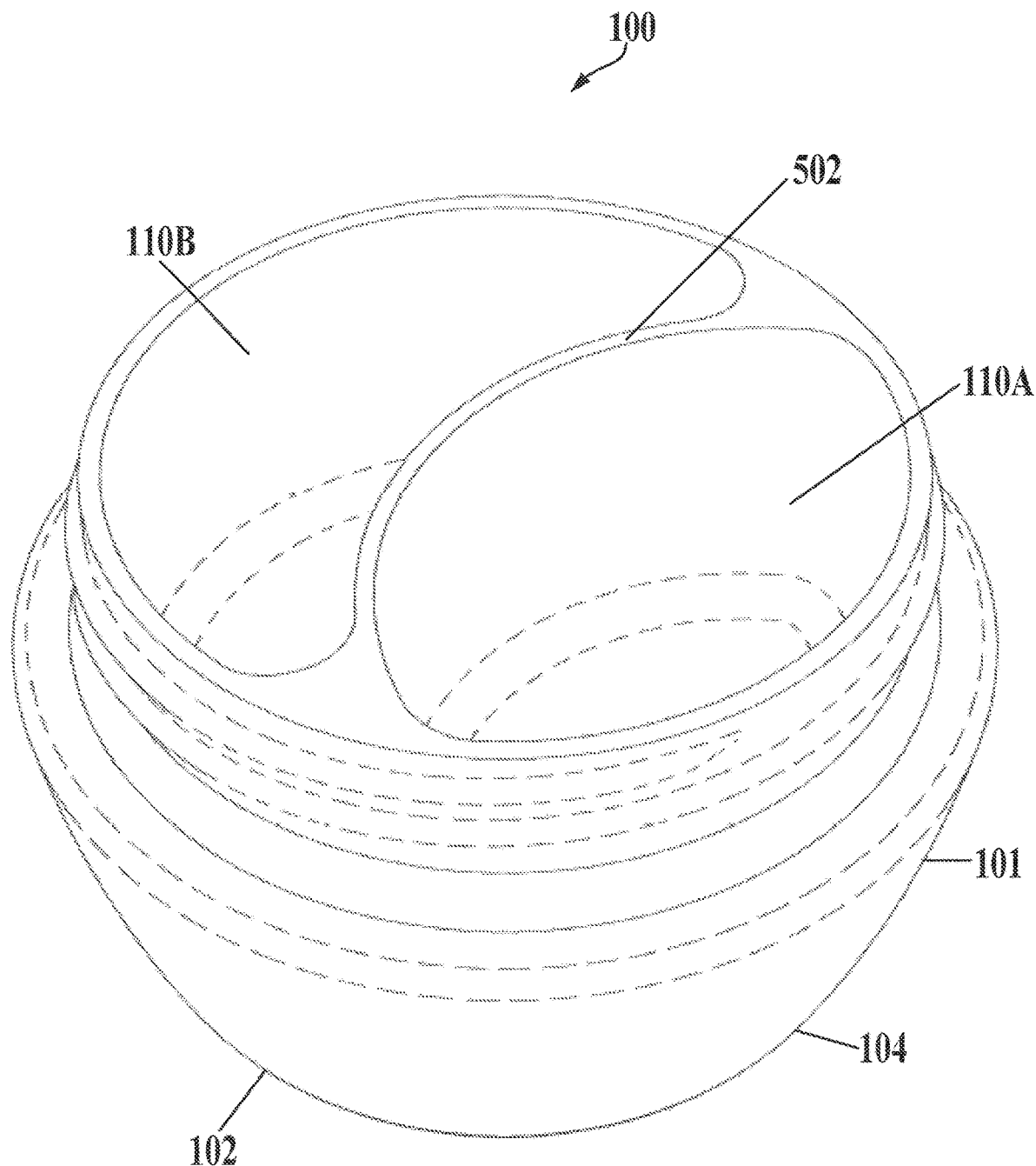
Figure 21A:
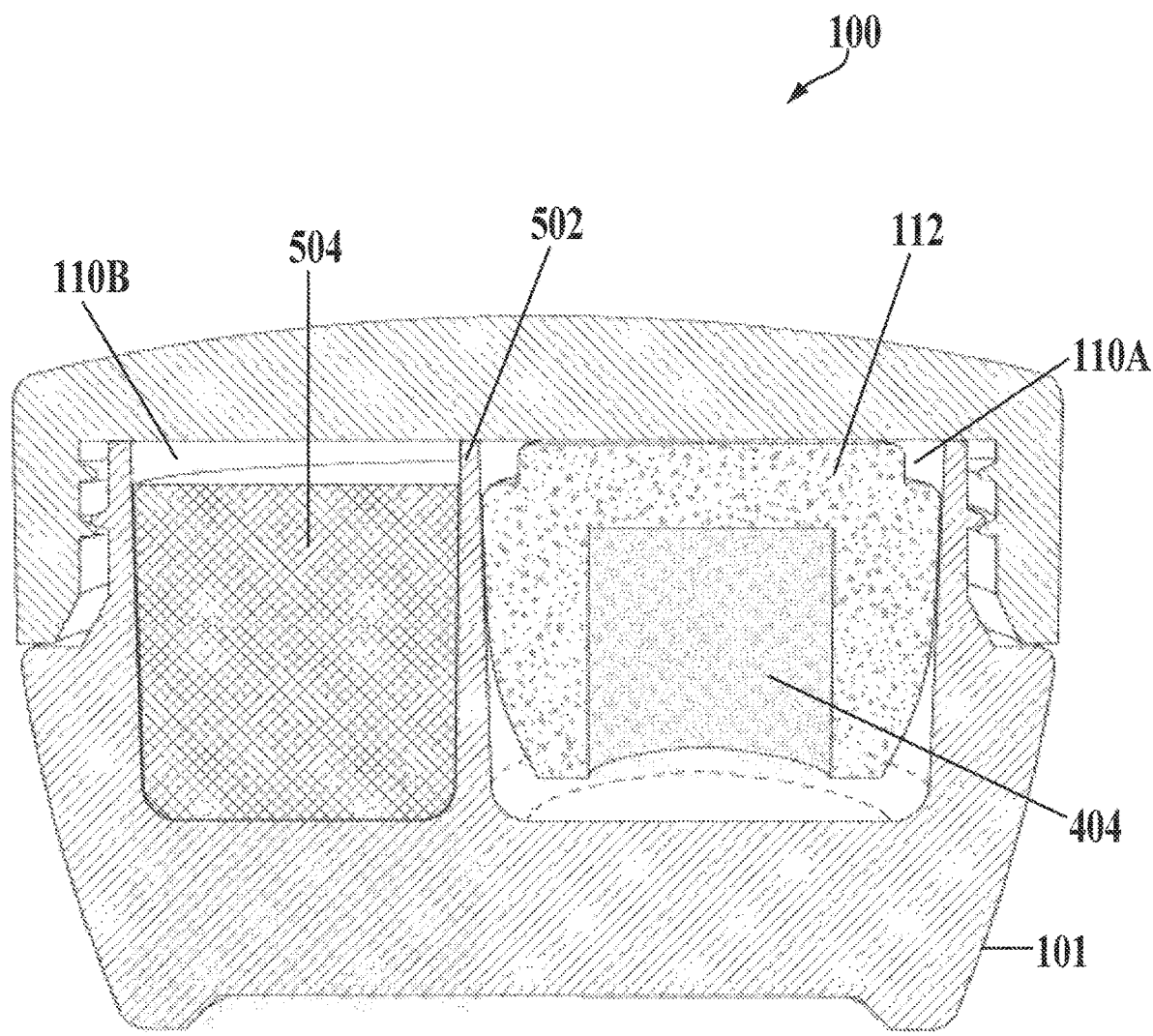
Figure 21B:
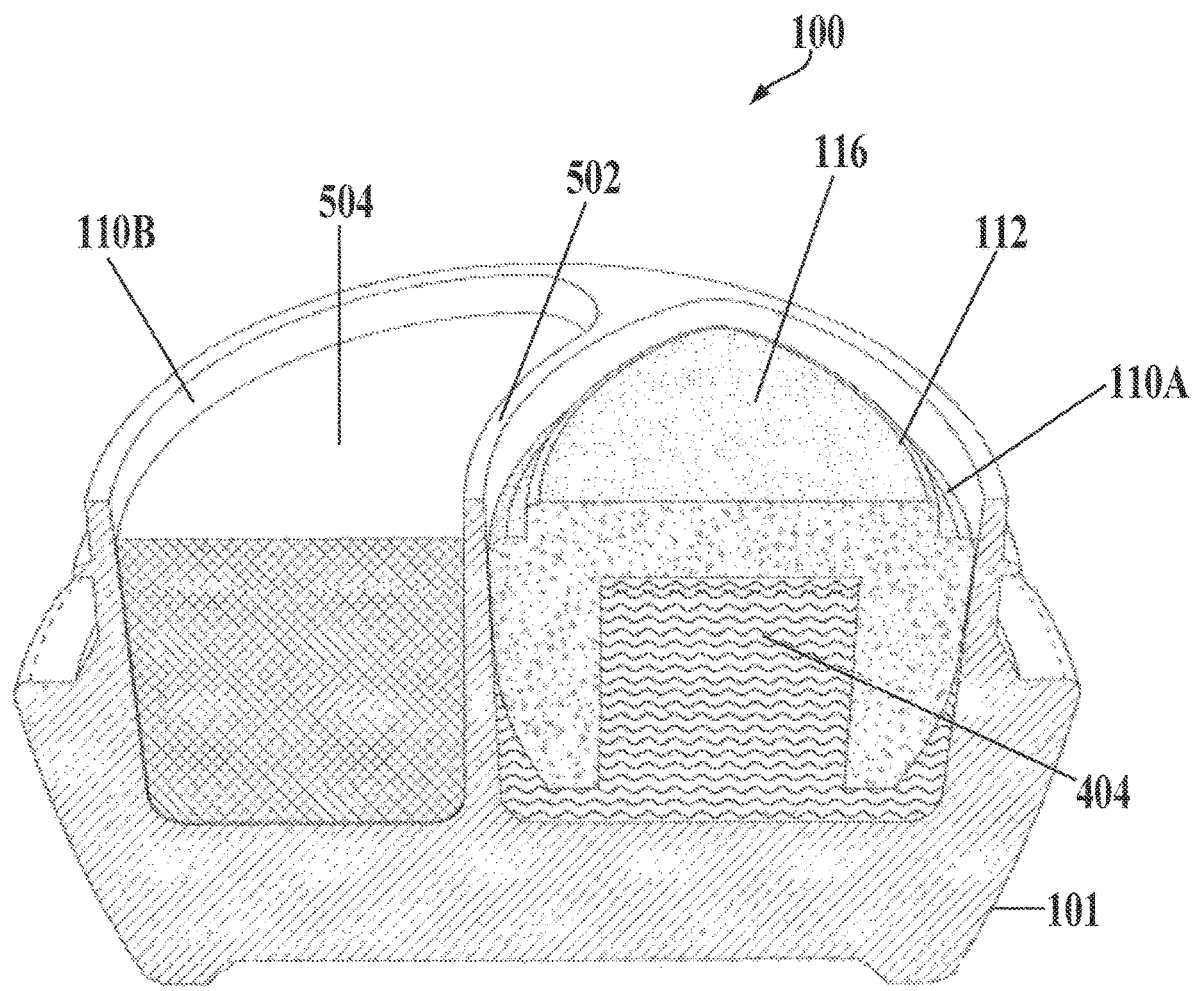

FIG. 19 illustrates the user wiping their finger along the top surface 116 of the porous applicator 112 to transfer dermatological agent from the porous applicator 112 to their finger, according to various embodiments of the present invention. As discussed above, the top surface 116 of the porous applicator 112 could have domes, recesses, and/or trough areas for facilitating this transfer of dermatological agent. FIG. 20 depicts the empty container 101 with empty reservoirs 110A, 110B prior to any insertion of dermatological agent and/or porous applicators 112, according to various embodiments of the present invention. FIGS. 21A-21B are cross-sectional views of the dispensing device 100 in the interior wall configuration, according to various embodiments of the present invention. In the sectional views, the cosmetic emulsion 504 is located in the second reservoir 110B on the left portion while the porous applicator 112 is located in the first reservoir 110A on the right portion. In FIG. 21A, the dermatological agent is not shown in the first reservoir 110A so that the porous applicator 112 is more visible, whereas in FIG. 21B the dermatological agent is shown in the first reservoir 110A.

As shown in both FIGS. 21A-21B, the porous applicator 112 can be cored out. In other words, as described above, the bottom of the porous applicator 112 can be cored out to create the cored portion 404, which increases the area of the first reservoir 110A that is available for liquid dermatological agent. FIG. 21B shows that the first reservoir 110A can hold more dermatological agent when the porous applicator 112 has the cored-out configuration. The porous applicator 112 can be cored out or not cored out, as appropriate. Also, the two dermatological agents contained in the first and second reservoirs, respectively, may complement or supplement each other. In particular, the two dermatological agents may mutually support the cosmetic or other benefits derived from their use.

Figure 22A:
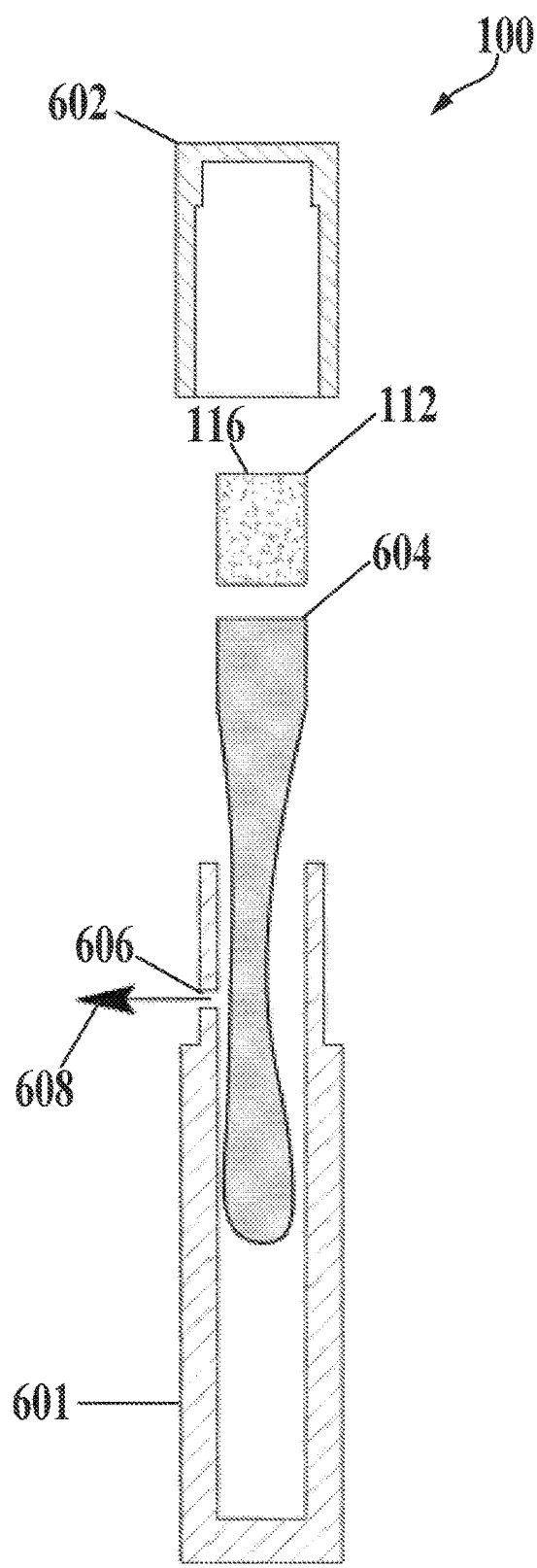

FIGS. 22A-23B show a bag-feed configuration of the dispensing device 100 according to various embodiments of the present invention. FIG. 22A is an exploded view of the dispensing device 100 comprising a cap 602 (similar to cap 106), the porous applicator 112, a bag 604, and a container 601 (similar to container 101, except that container 601 is preferably rigid), according to various embodiments of the present invention. The bag 604 has an opening at the top end but is otherwise sealed; the bag 604 also contains a liquid dermatological agent. The porous applicator 112 is inserted, at least partially, into the opening in the bag 604 to seal the opening in the bag to create a vacuum. The vacuum and the capillary/wicking action of the porous applicator 112 draws the liquid dermatological agent in the bag 604 to the top surface 116 of the porous applicator so that the liquid dermatological agent in the bag 604 can be applied to a user's skin by contacting the top surface 116 of the porous applicator 112 to the desired portion of the user's skin. By sealing the opening, the porous applicator 112 creates a vacuum in the bag 604 by absorption of the liquid by the open-celled pores of the porous applicator 112 that prevents the liquid from leaking out of the bag 604. The cap 602 also contributes to the vacuum by closing the opening 606 in the container 601. The cap 602 also prevents or reduces the accumulation of dust on the top surface 116 of the porous applicator 112. The capillary action of the porous applicator 112 draws the liquid dermatological agent from the bag 604, thereby creating an internal vacuum inside the bag 604. This internal vacuum may result based on ambient air particles being unable to penetrate the saturated porous applicator 112 and the unsaturated pores at the bottom of the porous applicator 112. Thus, ambient air particles cannot replace the dispensed liquid. Because the top surface 116 of the porous applicator 112 continues to have pores that are saturated from liquid wicking upwards through the porous applicator 112 while the bottom portion of the porous applicator has unsaturated pores, the internal vacuum occurs.

This eventually causes the capillary action of the dispensing device 100 to slow down. In other words, some of the pores begin to clog the dispensing device 100, resulting in a vacuum-lock effect. The vacuum-lock effect may be augmented for higher viscosity liquid dermatological agents because more viscous liquids tend to seal pores more acutely. The bag 604 held within the container 601 may address this vacuum-lock effect. In particular, the bag 604 is coupled to the porous applicator 112 such that liquid held inside the bag 604 wicks upwards through the porous applicator 112 to replenish the liquid dermatological agent dispensed via the porous applicator 112. No return of ambient air through the porous applicator 112 is necessary for the liquid in the bag 604 to continue experiencing capillary action. That is, the bag 604 may progressively collapse, shrivel, or otherwise reduce in size as liquid in the bag 604 continues to wick upwards through the porous applicator 112, even as little to no ambient air replenishes the empty pores of the porous applicator 112 that have dispensed liquid.

Figure 22B:
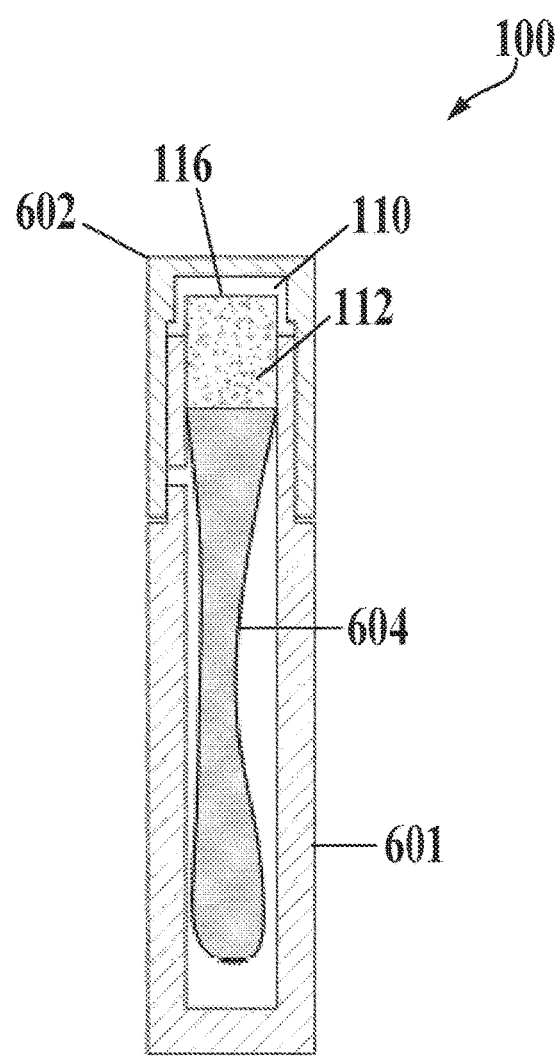

However, ambient air may flow through an air vent 606 into the interior of the rigid container 601. In this way, the ambient air replaces the volume ceded by the collapsing bag 604 as liquid wicks out of the bag 604. As shown in FIG. 22A, the air vent 606 can be a sidewall air vent defined by the rigid container 601. Additionally, FIG. 22A has an arrow 608 that illustrates the direction that air particles escape when the bag 604 is initially being filled with liquid. In contrast, FIG. 22B shows the cap 602 attached to the rigid container 601, which causes the cap 602 to seal or close the air vent 606. The cap 602 is removably attachable to the container 601 by, for example, a snug friction fit for attachment and a dislocating squeezing and upward force for detachment. Also, the rigid container 601 defines an opening that houses the bag 604. The container 601 is preferably rigid so that squeezing the container 601 does not cause the internal bag 604 to be squeezed. The porous applicator 112 also can be partially disposed in this opening. Aside from the rigid container 601 opening, the bag 604 also can have an opening at a proximate end. The proximate end refers to the end of the bag 604 closest to the cap 602. The porous applicator 112 may substantially fill the opening of the bag 604 so that liquid in the bag 604 is prevented from free-flowing out of the bag 604. As discussed above, this liquid is drawn out of the bag 604 into the porous applicator 112 and eventually to the top surface 116 via capillary action. The bag 604 may be a plastic bag made of a suitable plastic material. The plastic material could be HDPE, LDPE, or linear LDPE. The bag 604 could also be made of other suitable materials.

The combination of the plastic bag 604 and sidewall air vent 606 may combine to advantageously address slower dispensing caused by the vacuum-lock effect. In particular, such a vented rigid container 601 with bag 604 enables the liquid therein to wick and dispense freely even as the bag 604 empties. However, a vented rigid container 601 may incur a greater risk of leaking. The pressure differential between the air molecules at the top of the porous applicator 112 and the pressure at the surface pores of the porous applicator 112 causes a net inward force which reduces or prevents liquid from leaking. Because air particles may freely enter and escape the air vent 606, at least when the cap 602 is removed, the vented rigid container 601 does not have the same air-pressure differential. Consequently, liquid may seep from the porous applicator 112 out of the dispensing device 100, particularly when the dispensing device 100 is inverted. In contrast, the air-pressure differential for a sealed rigid container 601 is the same and causes the same net inward force as discussed above. In other words, even with the introduction of the bag 604 inside the container, the sealed rigid container 601 with the bag 604 does not leak or reduces leaking. Accordingly, the cap 602 may usefully enable the bag-feed configuration dispensing device 100 to switch between a vented and sealed configuration, depending on when the cap 602 is in the detached and attached configuration, respectively. FIG. 22A illustrates that the cap 602 does not seal or block the sidewall air vent 606 in the open configuration while FIG. 22B illustrates that the cap 602 seals or block the sidewall air vent 606 in the closed configuration.

Figure 23A:
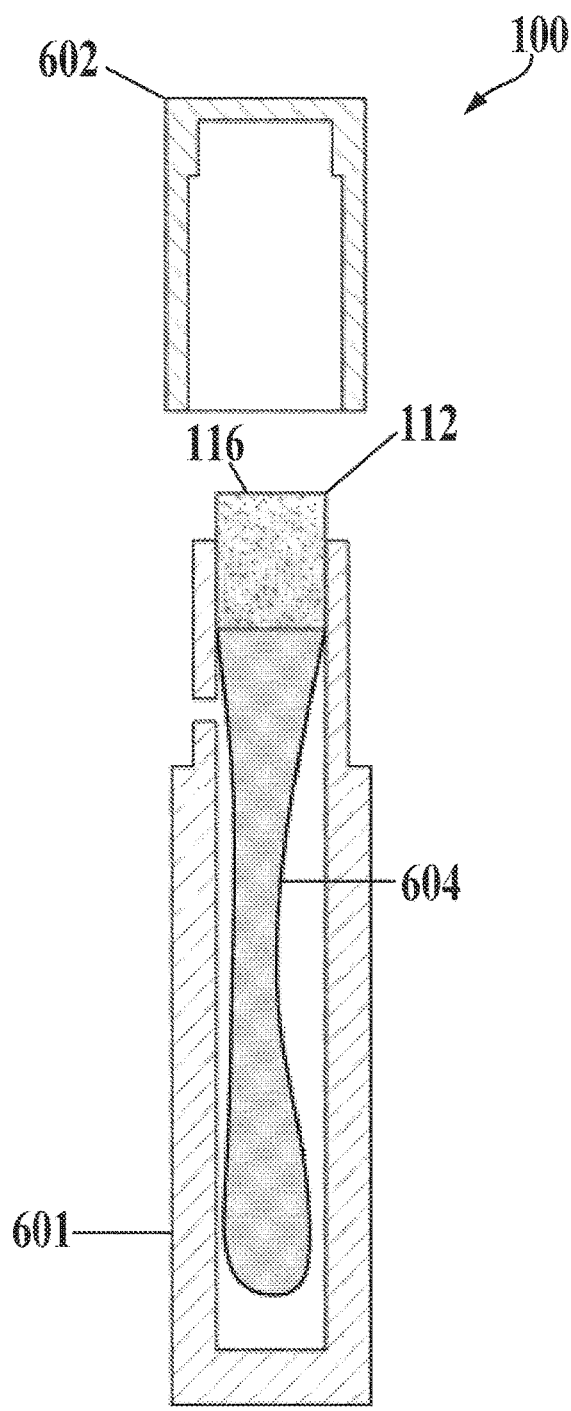
Figure 23B:
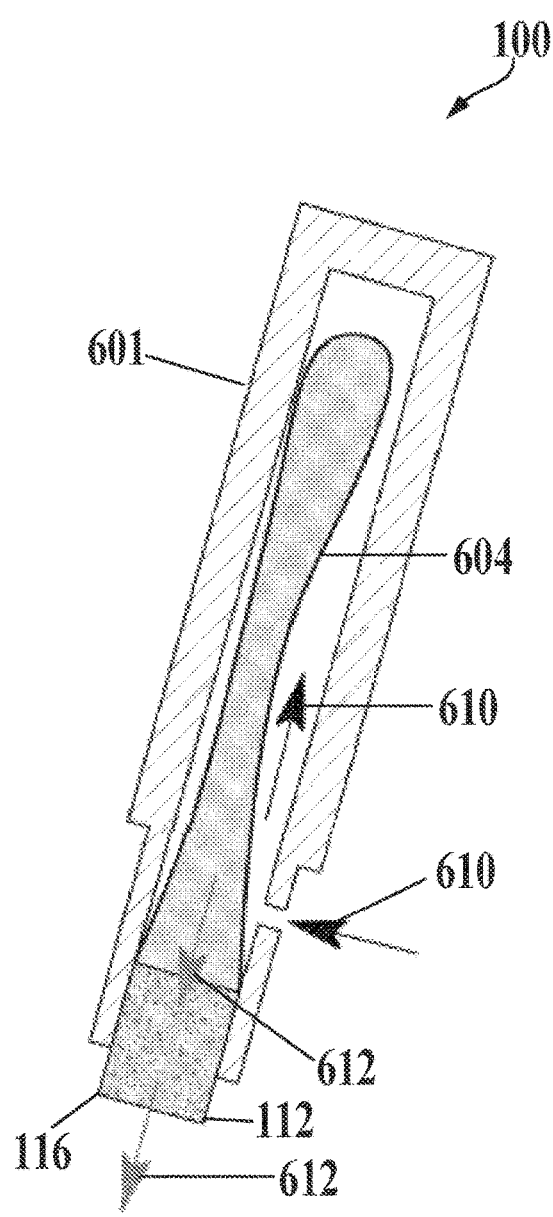

FIG. 23B shows the bag-feed configuration dispensing device 100 in an inverted position according to various embodiments of the present invention. The arrows 610 illustrate the direction that air flows into the container 601 to fill the volume previously occupied by the bag 601 as liquid from the bag 601 wicks through the porous applicator 112. Also, the arrows 612 illustrate the direction that the liquid from the bag 604 and the porous applicator 112 wicks in order to dispense the liquid. Preferably, the cap 604 is in the open configuration during use of the dispensing device 100 and in the closed configuration during shipping and storage. In this way, the bag-feed configuration dispensing device 100 enables free-flowing dispensing in use and prevents leaking during shipping and storage. The air vent 606 also advantageously allows efficient insertion and filling the bag 604, since when the bag 604 is inserted into the container 601 and liquid is being poured into the bag 604, air displaced by the filling bag 604 can escape the internal volume of the container 601 through the air vent 606. Also, the plastic (e.g., polyethylene) bag 604 could be used in other dispensing device 100 configurations, such as the fountain configuration dispensing device 100 shown in FIGS. 13A-13B, 14, 15A-15B, and 16 and the pre-saturated porous applicator configuration dispensing device 100 shown in FIGS. 24A-24C, 25A-25B, 26A-26B, and 27. Specifically, for a reservoir 110 that has a porous applicator 112, a polyethylene bag may hold the liquid dermatological agent therein and a lower portion of the porous applicator 112 to facilitate dispensing the liquid dermatological agent from the porous applicator 112 as the amount of dermatological agent in the reservoir 110 decreases.

FIGS. 24A-24C, 25A-25B, 26A-26B, and 27 show a pre-saturated porous applicator configuration of the dispensing device 100 according to various embodiments of the present invention. In this configuration, unlike other configurations described herein, the porous applicator 112 is not sitting in and filling up a container that contains a liquid dermatological agent. Instead, the porous applicator 112 is pre-saturated or infused with the liquid dermatological agent, and its capillary action continuously wicks the liquid dermatological agent to the top surface 116 of the porous applicator 112 until the liquid dermatological agent is spent.

Figures 25A, 25B:
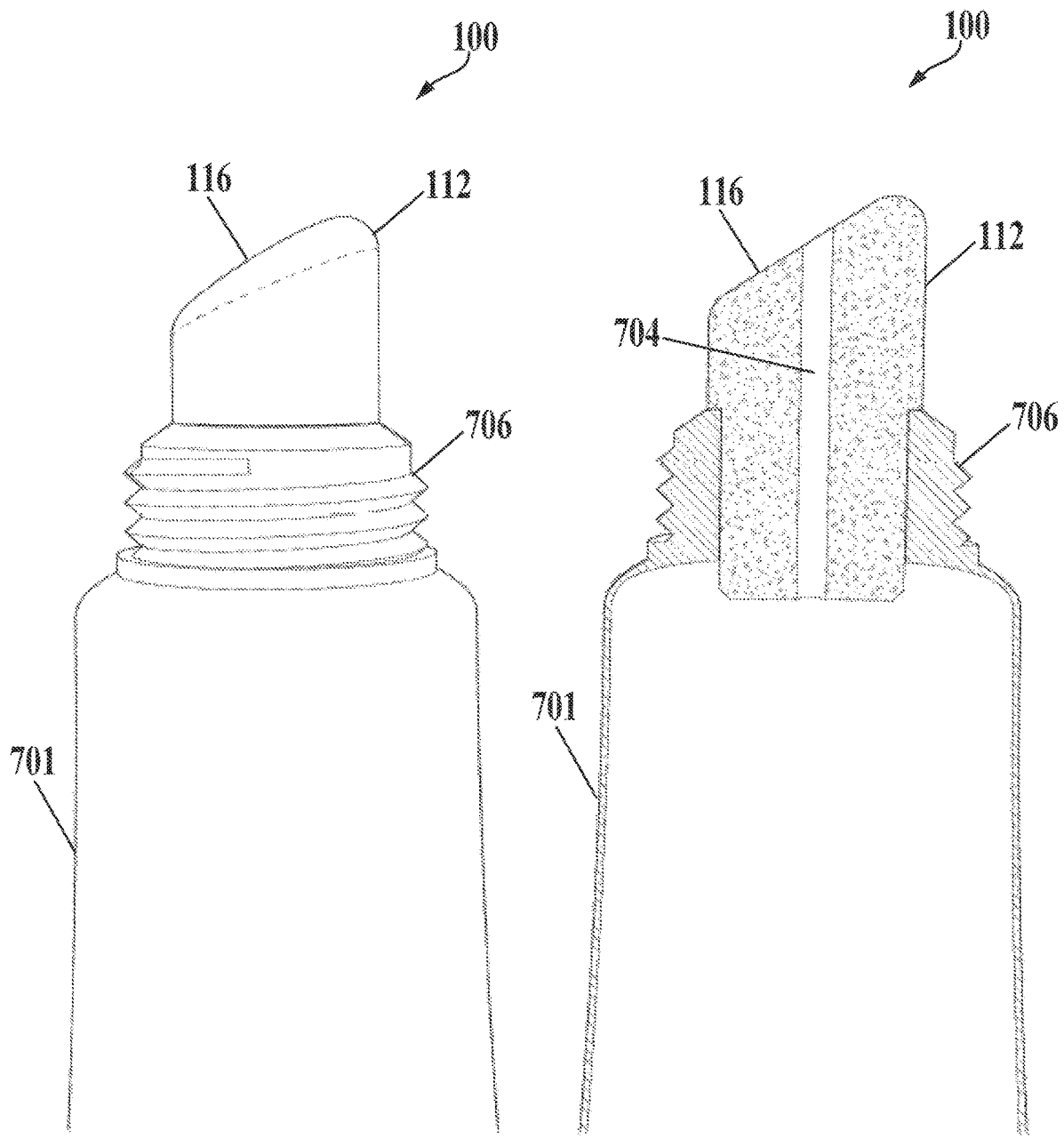

The top surface 116 of the porous applicator 112 in the pre-saturated porous applicator configuration may be slanted (relative to the axis of the container 701), as shown in FIGS. 25A-B, or it may be flat. A slanted top surface 116 may allow for an improved, smoother dispensing of the dermatological agents both saturating the porous applicator 112 and in the container 701 onto specific body parts of the user, such as the user's lips or skin. Specifically, the pre-saturated porous applicator configuration dispensing device 100 can enable a user to dispense two dermatological agents simultaneously using the porous applicator 112, with a main dermatological agent (squeezed from container 701) layered on top of a secondary dermatological agent (contained within the porous applicator 112). The secondary dermatological agent may be a lubricating layer formed on the top surface 116 of the porous applicator 112. The main and secondary dermatological agents could complement or supplement each other's dermatological or cosmetic effect. Application of the pre-saturated porous applicator configuration dispensing device 100 may be more comfortable and softer than conventional applicators of dermatological agent. Moreover, the pre-saturated porous applicator configuration dispensing device 100 may achieve better dermatological agent spreading performance, such as by increasing the smoothness and distribution of the layered main and secondary dermatological agents to be dispensed.

Figure 24A:
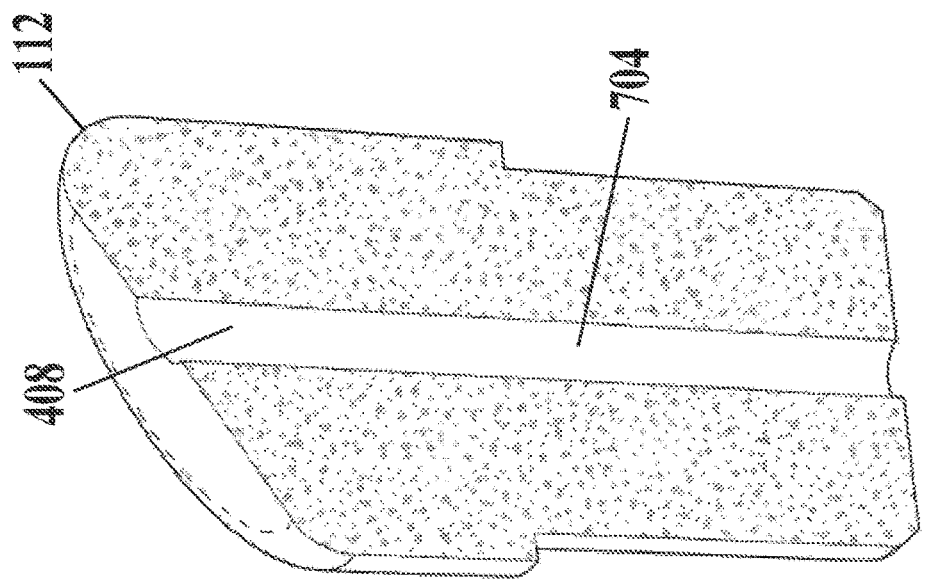
Figure 24B:
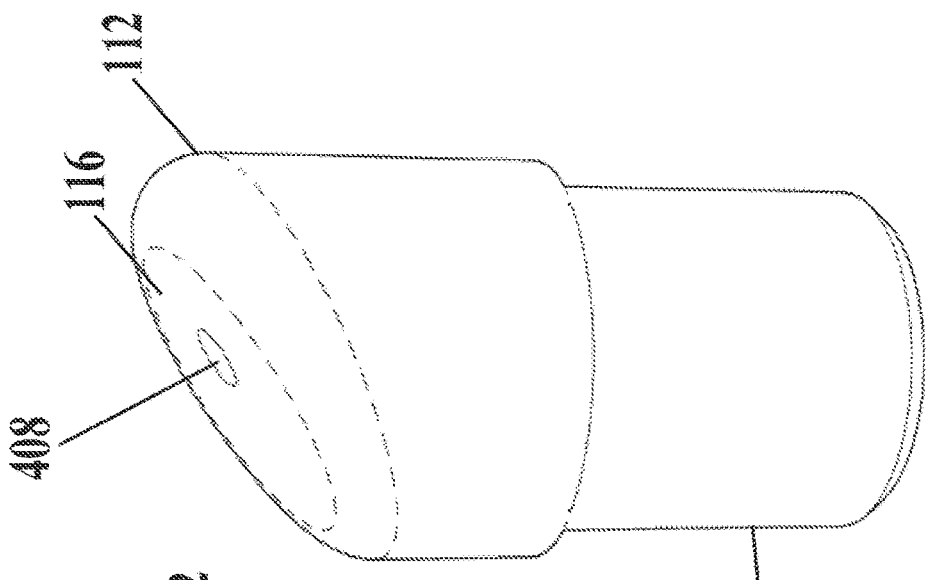

In such embodiments, the porous applicator 112 may be in the form of an applicator nib, as shown in FIGS. 24A-B. The porous applicator 112 comprises a lower tapered body portion 702 that is designed to fit within a tapered receiving portion of the flexible container 701 to hold the porous applicator 112 in place relative to the container 701. The tapered receiving region may define a threaded portion 706 (see FIGS. 25A-B, 26A-B and 27) for receiving a threaded cap (not shown) that, when in place, would cover the porous applicator 112.

Figure 24C:
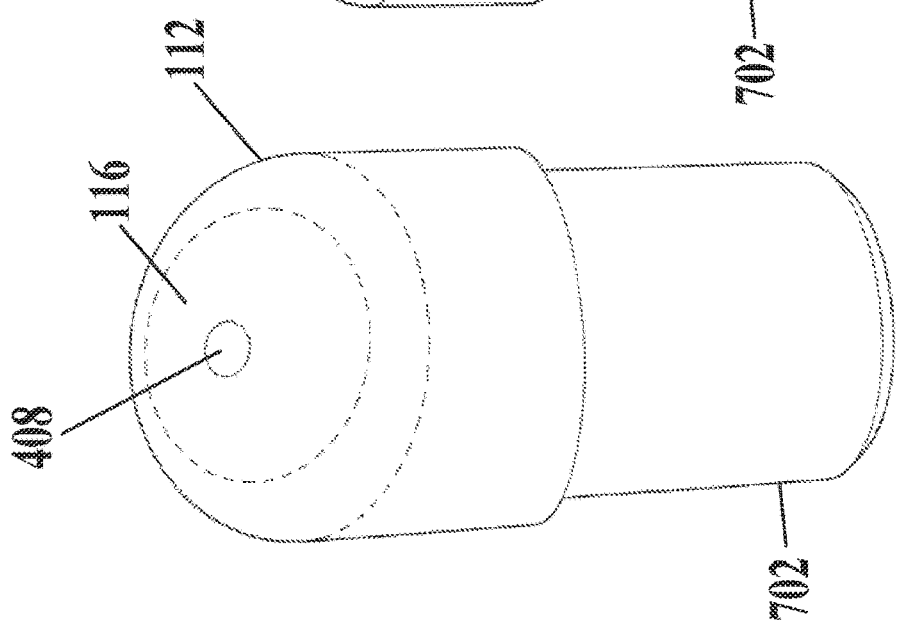

As shown in FIGS. 24A-24C, the porous applicator 112 comprises an orifice 408 which is coupled to the channel 704, which spans through the porous applicator 112 from top to bottom. The orifice 408 is at the terminal (top) end of the channel 704. Also as depicted in FIGS. 24A-24C, the top surface 116 of the porous applicator 112 can be inclined or slanted, relative to the axis of the container 701, although in other embodiments it can be flat. The configuration for the top surface 11 may be selected for aesthetic, functional, or other reasons such as to ensure a shape that is specifically tailored for applying the liquids infused in the porous applicator 112 and in the container 701. For example, a slanted top surface 116 could be used cosmetic lip products. In comparison to conventional products, the top surface 116 of the porous applicator 112 may act as a softer and more comfortable application surface for the user's lips (or other body parts). The container 701 could be made of a flexible, pliable material, such as a flexible, pliable plastic, so that squeezing the container 701 causes the liquid dermatological agent in the container 701 (which is preferably different from the liquid dermatological agent that saturates the porous applicator 112) to flow through the channel 704 of the porous applicator 112 and through the orifice 408, to the top surface 116.

As mentioned above, the porous applicator 112 is preferably saturated with a second dermatological agent that is different from the first dermatological agent in the container 701. This second dermatological agent may be a catalyst, enhancer, booster, or fragrance, for example. The first dermatological agent may be gel, balm, serum, ointment or some other suitable dermatological agent. Preferably, the second dermatological agent supplements or is otherwise a complimentary ingredient to the first dermatological agent in the flexible container 701. During application of the dispensing device 100, the second dermatological agent can create a lubricating layer on the top surface 116 to facilitate dispensing of the first dermatological agent. In particular, the lubricating layer of second dermatological agent can result in a smoother flow of the first dermatological agent.

FIG. 24C is a cross sectional view of the porous applicator 112 in which the channel 704 is visible, according to various embodiments of the present invention. The channel 704 is provided to enable the dermatological agent contained within the container 701 to flow through the channel 704 and orifice 408 to be dispensed, such as onto the user's lips. The porous applicator 112 preferably does not leak unless the porous applicator 112 contacts another porous surface like the user's lips. The second dermatological agent could be located in the applicator nib. Put differently, the porous applicator 112 can be saturated with the second dermatological agent.

Figures 26A, 26B:
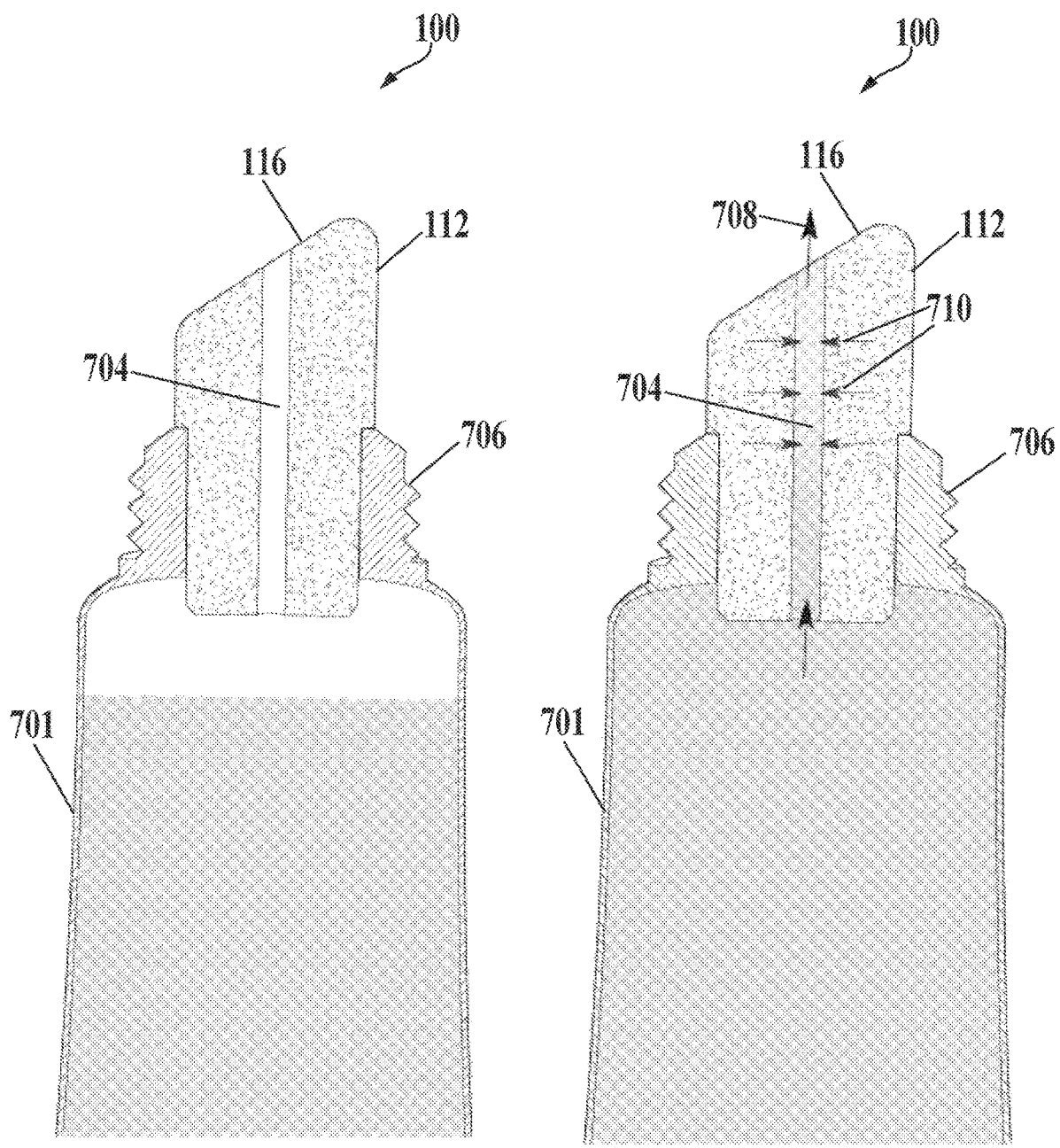

FIGS. 25A-25B depict the pre-saturated porous applicator configuration dispensing device 100 with the porous applicator 112 assembled in a tube package according to various embodiments of the present invention. That is, the porous applicator 112 is connected to flexible container 701 via the threaded portion 706. The porous applicator 112 can be shaped to snugly fit into the threaded portion 706. Additionally or alternatively, the porous applicator 112 may be otherwise molded into the threaded portion 706 so that porous applicator 112 and flexible container 701 form an integrated pre-saturated porous applicator configuration dispensing device 100. FIG. 25B illustrates how the first dermatological agent can flow through the channel 704 and orifice 408 onto the top surface 116. In this way, the first dermatological agent may flow over or on top of the layer of second dermatological agent, upon application of a squeezing force. FIGS. 26A-26B are sectional views of the pre-saturated porous applicator configuration dispensing device 100 according to various embodiments of the present invention. FIG. 26B illustrates squeezing the first dermatological agent onto the top surface 116. In FIG. 26A, the first dermatological agent is in a resting position inside the flexible container 701. In FIG. 26B, the first dermatological agent is being forced through the channel 706 and orifice 408, as illustrated by arrows 708. As the first dermatological agent flows through the channel 706, traces of the secondary dermatological agent may mix or combine with the main dermatological agent. Specifically, some amount of second dermatological agent may pass through from the pores adjacent the channel 706 into the channel 706.

Figure 27:
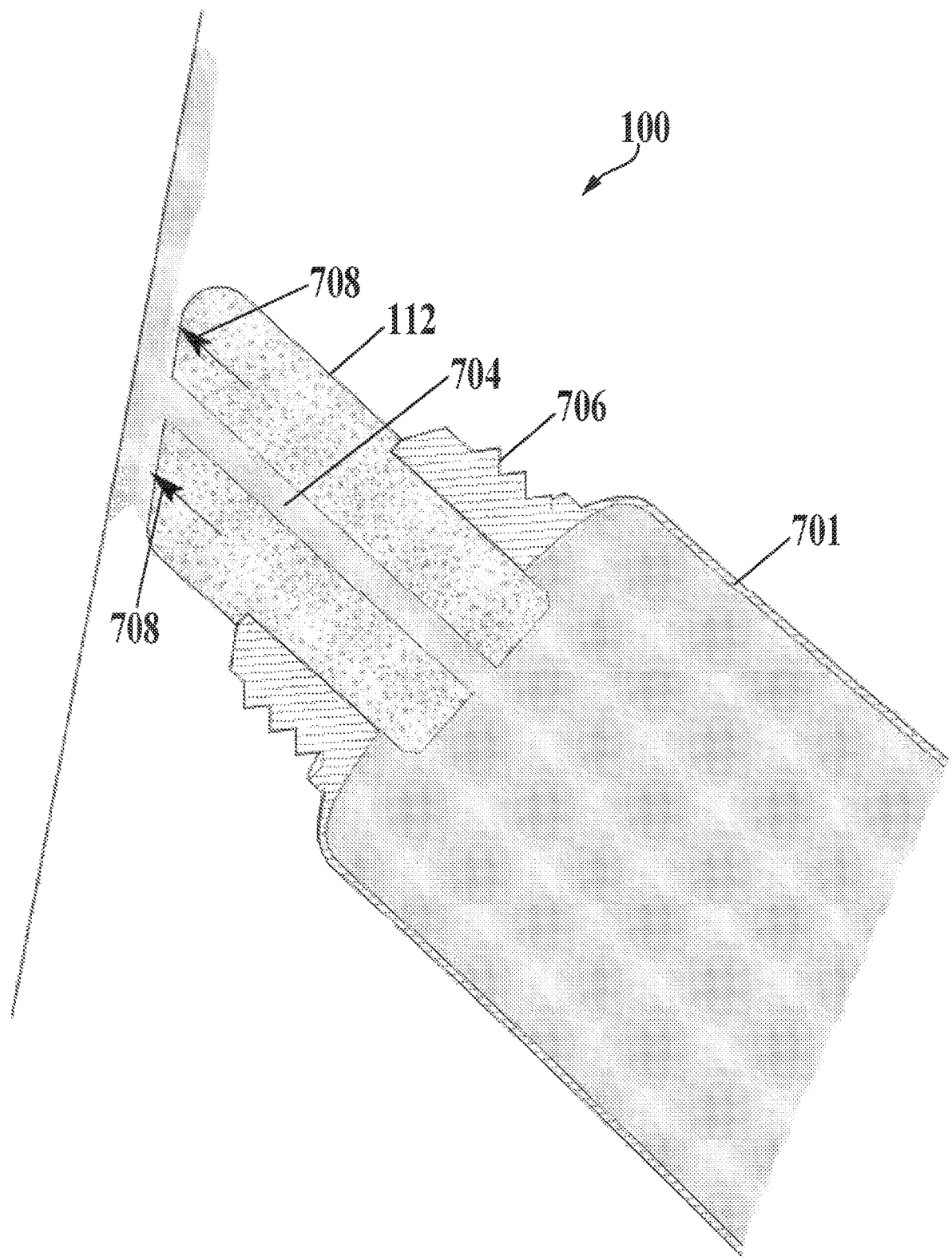

As can be seen in FIGS. 26A-26B, the porous applicator 112 is saturated with the second dermatological agent. The porous applicator 112 may be pre-saturated such that the second dermatological agent is in the porous applicator 112 prior to the first use of the dispensing device 100 by the user. FIG. 27 illustrates dispensing of the pre-saturated porous applicator configuration dispensing device 100 according to various embodiments of the present invention. As illustrated by FIG. 27, a lubricating layer of second dermatological agent is on the top surface 116 while first dermatological agent is squeezed through the orifice 408 so that the first dermatological agent flows over the second dermatological agent.

In one general aspect, therefore, the present invention is directed to a dispensing device that comprises a first container 101, 206 having a sidewall 104 that defines a reservoir 110. The first container has an upper opening to the reservoir at a top of the first container. And there is a first liquid in the reservoir, where the first liquid comprises a dermatological agent. A porous applicator 112 is in the reservoir. The porous applicator comprises open-celled pores that extend from a bottom of the porous applicator to a top surface of the porous applicator, such that the open-celled pores are filled with the first liquid such that the pores deliver the first liquid to the top surface of the porous applicator by capillary action, and such that the porous applicator substantially fills the reservoir and the upper opening at the top of the first container such that the first liquid is prevented from free-flowing out of the reservoir.

In various implementations, the upper opening of the first container is the only opening of the first container. And the porous applicator delivers the first liquid to the top surface of the porous applicator without use of a pump or buffer.

In other various implementations, the sidewall of the first container comprises an upper lip (or neck portion), and the dispensing device further comprises a cap 106, 208 that comprises a downward facing sidewall for engaging the upper lip (or neck portion) of the first container such that the cap is detachably removable from the first container to reveal the porous applicator.

In still other implementations, the dispensing device comprises a second container 204, e.g., a squeeze tube, containing a second liquid. The second liquid may comprise a second dermatological agent that is different from the first liquid; the second container may have a circular, threaded post 212 at an upper end of the second container; the first container comprises a circular post 214 that extends upward from a lower, central portion of the first container into the reservoir; the circular post of the first container comprises a downward-facing threaded recess 216 for receiving the threaded post of the second container such that first container is detachably removable from the second container by unscrewing the first container. The first container may comprise a hard, rigid plastic and the second container may comprise a pliable plastic.

In various implementations, the circular post of the first container comprises an upper wall that blocks the second liquid from entering the reservoir defined by the first container. In other embodiments, the threaded post of the second container comprises a tip that extends from the threaded post of the second container into the porous applicator when the first container is attached to the second container. In such embodiments, the tip can comprise an opening for dispensing the second liquid that is in the second container. The upper (or distal) end of the tip can terminate below or at the top surface of the porous applicator when the threaded post of the second container is fully threaded into the circular post of the first container. Also, the cap can comprise a downward facing pintle that is inserted into the opening of the tip of the second container when the cap is attached to the first container the threaded post of the second container is fully threaded into the circular post of the first container.

In other general aspects, the present invention is directed to a dispensing device that comprises: a first container that defines a reservoir; a liquid dermatological agent in the reservoir; a porous applicator in the reservoir; and a second container containing a powder. The porous applicator comprises an injection-molded polyethylene body having open-celled pores that extend from a bottom of the porous applicator to a top surface of the porous applicator, where the open-celled pores are filled with the liquid such that the pores deliver the liquid to the top surface of the porous applicator by capillary action. The second container is attached to the first container and comprises a nozzle that extends to an orifice in a top surface of the porous applicator. The nozzle comprises an opening for dispensing the powder that is in the second container through the orifice and onto the top surface of the porous applicator.

In various implementations, the powder comprises a glitter. Also, the porous applicator may have a domed top surface. In addition, the second container may comprise a pliable material, such that the powder is caused to be dispensed through the nozzle and onto the top surface of the porous applicator when the second container is squeezed. Still further, the dispensing device may further comprise a lid that is removably coupled to the first container. The lid, when coupled to the first container, defines a space between an under surface of the lid and the top surface of the porous applicator such that when the powder is dispensed through the nozzle, the powder is about the space and settles onto the top surface of the porous applicator. In addition, the lid may further comprise a pintle for closing the orifice in the top surface of the porous applicator. Additionally, the second container may comprise a threaded post at an upper end of the second container that is securable to a threaded recess defined by the first container, such that the first container is detachably removable from the second container.

In another general aspect, the dispensing device comprises: a first container having a sidewall and one or more interior walls, which collectively define a plurality of reservoirs, including at least a first reservoir and a second reservoir; a first liquid dermatological agent in the first reservoir; and a first porous applicator in the first reservoir. The first porous applicator comprises an injection-molded polyethylene body having open-celled pores, where the open-celled pores extend from a bottom of the first porous applicator to a top surface of the first porous applicator, and where the open-celled pores are filled with the first liquid such that the pores deliver the first liquid to the top surface of the first porous applicator by capillary action without externally-applied pressure, and where the first porous applicator substantially fills the first reservoir such that the first liquid is prevented from free-flowing out of the first reservoir.

In various implementations, the dispensing device further comprises a second dermatological agent in the second reservoir. Also, the dispensing device may further comprise a second porous applicator in the second reservoir. The second dermatological agent may be a cream or lotion, for example. The dispensing device may further comprise a polyethylene bag in the first reservoir. As such, the first liquid dermatological agent may be in the polyethylene bag; and the first porous applicator may be partially disposed in the polyethylene bag. Also, the top surface may be a non-flat surface to define a dosage.

In yet other general aspects, the dispensing device may comprise: a plastic bag containing a liquid dermatological agent, where the plastic bag comprises a closed distal end and an opening at a proximate end; and a porous applicator inserted into the opening at the proximate end of the plastic bag. The porous applicator has an upper portion that extends past a top of the proximate end of the plastic bag; the porous applicator comprises an injection-molded polyethylene body having open-celled pores; the open-celled pores extend from a bottom of the porous applicator to a top surface of the porous applicator; the porous applicator draws the liquid in the plastic bag such that the open-celled pores are filled with the liquid such that the pores deliver the liquid to a top surface of the porous applicator by capillary action; and the porous applicator substantially fills the opening at the proximate end of the plastic bag such that the liquid is prevented from free-flowing out of the plastic bag.

In various implementations, the plastic bag comprises a plastic material selected from the group consisting of high-density polyethylene, low-density polyethylene, and linear low-density polyethylene. Also, the dispensing device may further comprise a rigid container that defines an opening that houses the plastic bag, where the porous applicator is at least partially disposed in the opening of the rigid container, and where the rigid container further defines a sidewall air vent to the opening of the rigid container.

In still other general aspect, the dispensing device comprises a container; a first liquid dermatological agent in the container; and a porous applicator partially inserted in an opening at a top end of the container. The porous applicator has a top surface that extends past the top end of the container. Also, the porous applicator is saturated with a second liquid comprising a second dermatological agent. And the porous applicator comprises an injection-molded polyethylene body having open-celled pores, where the open-celled pores extend from a bottom of the porous applicator to a top surface of the porous applicator, and where the open-celled pores are filled with the second dermatological agent such that the pores deliver the second dermatological agent to the top surface of the porous applicator by capillary action without externally-applied pressure. Also, the porous applicator defines a channel from a bottom surface of the porous applicator to the top surface of the porous applicator, such that the first dermatological agent can flow through the channel in the porous applicator over the top surface of the porous applicator.

In various implementations, the first container is pliable such that upon receiving, by the first container, a squeezing force, the first dermatological agent flows through the channel in the porous applicator to the top surface of the porous applicator. Also, the top surface of the porous applicator may be slanted or flat relative to the opening of the container. Still further, the top end of the container may comprise a tapered receiving portion to secure the porous applicator.

The dermatological agents of the first and second liquids can be cosmetic, fragrance, or pharmaceutical dermatological agents, such as cosmetic or pharmaceutical creams, fragrances, oils, lotions, etc.

Although various embodiments have been described herein, many modifications, variations, substitutions, changes, and equivalents to those embodiments may be implemented and will occur to those skilled in the art. For example, where example materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the inventions described herein. The foregoing description of the embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A dispensing device comprising:
   a plastic bag containing a liquid dermatological agent, wherein the plastic bag comprises a closed distal end and an opening at a proximate end; and
   a porous applicator inserted into the opening at the proximate end of the plastic bag such that:
   the porous applicator has an upper portion that extends past a top of the proximate end of the plastic bag;
   the porous applicator comprises an injection-molded polyethylene body having open-celled pores;
   the open-celled pores extend from a bottom of the porous applicator to a top surface of the porous applicator;
   the porous applicator draws the liquid dermatological agent in the plastic bag such that the open-celled pores are filled with the liquid dermatological agent such that the pores deliver the liquid dermatological agent to a top surface of the porous applicator by capillary action; and
   the porous applicator substantially fills the opening at the proximate end of the plastic bag such that the liquid dermatological agent is prevented from free-flowing out of the plastic bag.

2. The dispensing device of claim 1, wherein the porous applicator has a domed top surface.

3. The dispensing device of claim 1, wherein the plastic bag comprises a plastic material selected from the group consisting of high-density polyethylene, low-density polyethylene, and linear low-density polyethylene.

4. The dispensing device of claim 1, further comprising a rigid container that defines an opening that houses the plastic bag, wherein the porous applicator is at least partially disposed in the opening of the rigid container, and wherein the rigid container further defines a sidewall air vent to the opening of the rigid container.

5. The dispensing device of claim 4, further comprising a lid that is removably coupled to the rigid container, wherein the lid, when coupled to the rigid container, encloses the porous applicator.

6. The dispensing device of claim 5, wherein the top surface of the porous applicator is configured to be applied to skin of a user of the dispensing device, to thereby apply the liquid dermatological agent to the skin of the user of the dispensing device.

7. The dispensing device of claim 6, wherein the lid covers the sidewall air vent when the lid is coupled to the rigid container.

8. The dispensing device of claim 7, wherein the liquid dermatological agent comprises a liquid dermatological agent selected from the group consisting of a gel, a balm, a serum and an ointment.

9. The dispensing device of claim 1, wherein the liquid dermatological agent comprises a liquid dermatological agent selected from the group consisting of a gel, a balm, a serum and an ointment.

* * * * *